United States Patent
El-Safty et al.

(10) Patent No.: US 9,187,343 B2
(45) Date of Patent: Nov. 17, 2015

(54) NANOSTRUCTURE MATERIAL SUPPORTING ARSENIC ION ADSORPTION COMPOUND AND METHOD TO REMOVE ARSENIC ION USING THE SAME

(75) Inventors: Sherif El-Safty, Tsukuba (JP); Ahmed Shahat Ahmed, Tsukuba (JP); Kohmei Halada, Tsukuba (JP); Mohamed Shenashen, Tsukuba (JP); Ahmed Abouelmagd, Tsukuba (JP); Hitoshi Yamaguchi, Tsukuba (JP)

(73) Assignee: National Institute for Materials Science (JP)

( * ) Notice: Subject to any disclaimer, the term of this patent is extended or adjusted under 35 U.S.C. 154(b) by 132 days.

(21) Appl. No.: 13/979,594

(22) PCT Filed: Jan. 12, 2012

(86) PCT No.: PCT/JP2012/050493
§ 371 (c)(1),
(2), (4) Date: Sep. 18, 2013

(87) PCT Pub. No.: WO2012/096346
PCT Pub. Date: Jul. 19, 2012

(65) Prior Publication Data
US 2014/0001125 A1    Jan. 2, 2014

(30) Foreign Application Priority Data

Jan. 14, 2011 (JP) .................... 2011-006345
Nov. 1, 2011 (JP) .................... 2011-240708

(51) Int. Cl.
*C02F 1/28* (2006.01)
*B82Y 30/00* (2011.01)
(Continued)

(52) U.S. Cl.
CPC ............ *C02F 1/281* (2013.01); *B01J 20/28007* (2013.01); *B01J 20/28057* (2013.01);
(Continued)

(58) Field of Classification Search
USPC ........................................... 210/688
See application file for complete search history.

(56) References Cited

U.S. PATENT DOCUMENTS

| 6,027,775 A | 2/2000 | Kasuga et al. |
| 2005/0029198 A1* | 2/2005 | Tepper et al. ................ 210/688 |

(Continued)

FOREIGN PATENT DOCUMENTS

| JP | H07-088482 A | 4/1995 |
| JP | H08-267053 A | 10/1996 |

(Continued)

OTHER PUBLICATIONS

P.B. Tchounwou, J.A. Centeno, A.K. Patlolla, "Arsenic toxicity, mutagenesis, and carcinogenesis—a health risk assessment and management approach", Molecular and Cellular Biochemistry 255, pp. 47-55, (2004) (in English).

(Continued)

*Primary Examiner* — Chester Barry
(74) *Attorney, Agent, or Firm* — Harness, Dickey & Pierce, P.L.C.

(57) ABSTRACT

Means for reducing an arsenic ion concentration in the solution to the degree of ultra trace amount are provided. Ammonium molybdate is supported by a nanostructure material by mixing the nanostructure material, which is obtained after the nanostructure material such as an alumina reacts with a surfactant, in the solution containing the ammonium molybdate. The nanostructure material supporting an arsenic ion adsorption compound such as ammonium molybdate can selectively adsorb and remove trace of arsenic ion in the solution by a room temperature treatment without a water conditioning such as pH control. In our removal system of arsenic, extra posttreatments are not needed because special pretreatments are not carried out, and special heating equipments are not used. Accordingly, our removal system of arsenic can be constructed at low cost. Furthermore, it can supply an arsenic-free solution by be constructed at multi stages.

39 Claims, 21 Drawing Sheets

(51) Int. Cl.
B01J 20/28 (2006.01)
B01J 20/32 (2006.01)
B01J 20/34 (2006.01)
G01N 21/78 (2006.01)
C02F 101/10 (2006.01)

(52) U.S. Cl.
CPC ...... *B01J20/28069* (2013.01); *B01J 20/28083* (2013.01); *B01J 20/3204* (2013.01); *B01J 20/3219* (2013.01); *B01J 20/3236* (2013.01); *B01J 20/3433* (2013.01); *B01J 20/3475* (2013.01); *B82Y 30/00* (2013.01); *C02F 1/288* (2013.01); *G01N 21/78* (2013.01); *C02F 2101/103* (2013.01); *C02F 2303/16* (2013.01); *C02F 2305/08* (2013.01)

(56) References Cited

U.S. PATENT DOCUMENTS

| 2005/0118722 | A1* | 6/2005 | Geen | 436/73 |
| 2005/0281734 | A1 | 12/2005 | Lee et al. | |
| 2008/0293976 | A1 | 11/2008 | Olah et al. | |
| 2011/0158872 | A1* | 6/2011 | Ariya | 423/219 |

FOREIGN PATENT DOCUMENTS

| JP | H09-327694 A | 12/1997 |
| JP | H10-137504 A | 5/1998 |
| JP | 10152323 A | 6/1998 |
| JP | 2000024647 A | 1/2000 |
| JP | 2000140626 A | 5/2000 |
| JP | 2000-176441 A | 6/2000 |
| JP | 2004301609 A | 10/2004 |
| JP | 2005-000747 A | 1/2005 |
| JP | 2005-046728 A | 2/2005 |
| JP | 2005535547 A | 11/2005 |
| JP | 2008538531 A | 10/2008 |
| JP | 2010500168 A | 1/2010 |
| WO | WO-2006/115486 A1 | 11/2006 |

OTHER PUBLICATIONS

M.F. Hughes, "Arsenic toxicity and potential mechanisms of action", Toxicology Letters 133, pp. 1-16, (2002) (in English).
P. Xin, C. Guoshu, "Inhibitory Kinetics Spectrophotometric Determination of Trace Arsenic V", Chinese Journal of Analytical Chemistry 31, pp. 38-40, (2003) (with English Abstract).
H. Matsunaga, C. Kanno, T. M. Suzuki, "Naked-eye detection of trace arsenic (V) in aqueous media using molybdenum-loaded chelating resin having β-hydroxypropyl-di (β-hydroxyethyl) amino moiety", Talanta 66, pp. 1287-1293, (2005) (in English).
C. Ludwig, M. Dolny, H.J. Gotze, "Fourier transform Raman and infrared spectra and normal coordinate analysis of organo-arsenic (III), -antimony (III) and -bismuth (III) thiolates", Spectrochimica Acta Part A 56, pp. 547-555 (2000) (in English).
C. Ludwig, M. Dolny, H.J. Gotze, "Fourier-transform Raman and infrared spectra and normal coordinate analysis of the triphenykl compounds and their methyl-, methoxy- and fluoro-substituted derivatives of arsenic, antimony and bismuth", Spectrochimica Acta Part A 53, pp. 2363-2372 (1997) (in English).
V. Dufailly, L. Noel, T. Guerin, "Optimisation and critical evaluation of a collision cell technology ICP-MS system for the determination of arsenic in foodstuffs of animal origin", Analytica Chimica Acta 611, p. 134-142, (2008) (in English).
R. Piech, W.W. Kubiak, "Determination of trace arsenic with DDTC-Na by cathodic stripping voltammetry in presence of copper ions", Journal of Electroanalytical Chemistry, pp. 1-6, (2006) (in English).
C. Lomonte, M. Currell, R.J.S. Morrison, I.D. McKelvie, S.D. Kolev, "Sensitive and ultra-fast determination of arsenic (III) by gas-diffusion flow injection analysis with chemiluminescence detection", Analytica Chimica Acta 583, pp. 72-77, (2007) (in English).
J. Michon, V. Deluchat, R.Al Shukry, C. Dagot, J.C. Bollinger, "Optimization of a GFAAS method for detemination of total inorganic arsenic in drinking water", Talanta 71, pp. 479-485, (2007) (in English).
C.G. Bruhn, C.J. Bustos, K.L. Saez, J.Y. Neira, S.E. Alvarez, "A comparative study of chemical modifiers in the determination of total arsenic in marine food by tungsten coil electrothermal atomic absorption spectrometry", Talanta 71, pp. 81-89 (2007) (in English).
X. Li, Y. Su, K. Xu, X. Hou, Y. Lv, "Simple and sensitive determination of arsenic by volatile arsenic trichloride generation atomic fluorescence spectrometry", Talanta 72, pp. 1728-1722 (2007) (in English).
A.L. Lindberg, W. Goessler, M. Grander, B. Nermell, M. Vahter, "Evaluation of the three most commonly used analytical methods for determination of inorganic arsenic and its metabolites in urine", Toxicology Letters 168, pp. 310-318 (2007) (in English).
Y.C. Yip, H.S. Chu, C.F. Yuen, W.C. Sham, "Determination of Inorganic Arsenic (III) and Arsenic (V) in Water Samples by Ion Chromatography/Inductively Coupled Plasma-Mass Spectrometry", Journal of AOAC International, vol. 90, No. 1, pp. 284-290 (2007) (in English).
Z.L. Zhu, J. Liu, S.H. Zhang, X. Na, X. Zhang, "Evaluation of a hydride generation-atomic fluorescence system for the determination of arsenic using a dielectric barrier discharge atomizer", Analytica Chimica Acta 607, pp. 136-141, (2008) (in English).
P. Heitland, H.D. Koster, "Fast Determination of Arsenic Species and Total Arsenic in Urine by HPLC-ICP-MS: Concentration Ranges for Unexposed German Inhabitants and Clinical Case Studies", Journal of Analytical Toxicology, vol. 32, pp. 308-314, (2008) (in English).
English Translation of the International Preliminary Report on Patentability (Chapter I of the Patent Cooperation Treaty), issued Jul. 16, 2013.

* cited by examiner

Fig. 5
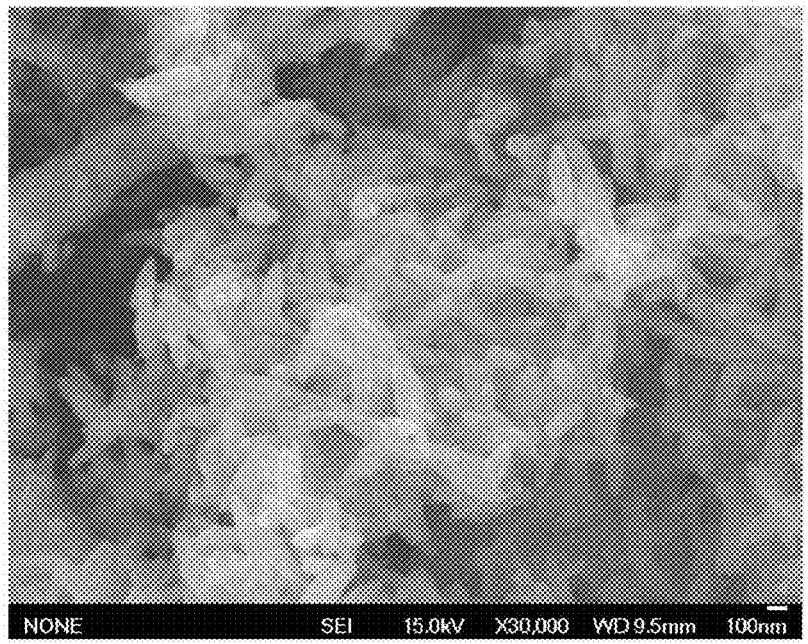
Fig. 6
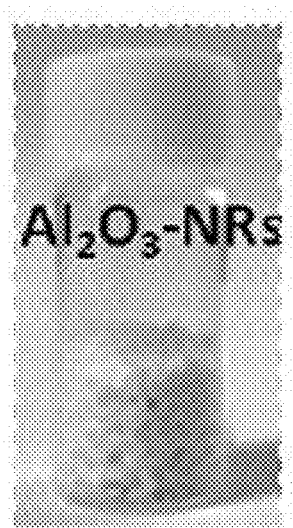
Alumina supporting
adsorption compound
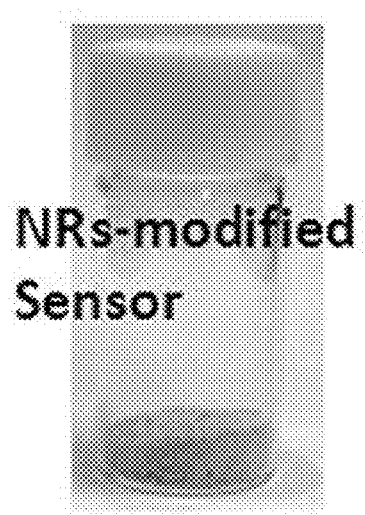
Material supporting
adsorption compound

| Initial As(V) concentration | As(V) concentration after using 25mg Alumina-captor | As(V) concentration removed by 25mg Alumina-captor | Removal Efficiency |
|---|---|---|---|
| 2.035ppm | 0.636ppm | 1.363ppm | 67% |

Fig. 26

| As(V) in Tap-water | As(V) added to Tap-water | As(V) concentration after using 20mg Alumina-Captor | As(V) removed by 20mg Alumina-Captor | Removal Efficiency |
|---|---|---|---|---|
| 0.0005ppm | 2.013ppm | 0.685ppm | 1.328ppm | 66% |

Fig. 27

|  | Sample A | Sample B | Sample C | Tap-Water |
|---|---|---|---|---|
| As(V) measured before treating | 0.0007 | 0.0002 | 0.0001 | 0.0005 |
| As(V) spiked to the sample | 2.013 | 2.011 | 2.014 | 2.010 |
| As(V) measured after treating | 0.2147 | 0.2185 | 0.2350 | 0.2183 |
| Removal Efficiency | 89.2% | 89.6% | 88.3% | 89.6% |

US 9,187,343 B2

NANOSTRUCTURE MATERIAL SUPPORTING ARSENIC ION ADSORPTION COMPOUND AND METHOD TO REMOVE ARSENIC ION USING THE SAME

CROSS-REFERENCE TO RELATED APPLICATIONS

This application is a U.S. 371 National Stage of International Application No. PCT/JP2012/050493, filed on Jan. 12, 2012 and published in Japanese as WO/2012/096346 A1 on Jul. 19, 2012. This application claims the benefit of Japanese Application Nos. 2011-006345, filed on Jan. 14, 2011 and 2011-240708, filed on Nov. 1, 2011. The disclosures of the above applications are incorporated herein by reference.

TECHNICAL FIELD

This invention is regarding a nanostructure, which has a regular array and a porous structure, supporting an arsenic ion adsorption compound that can adsorbs selectively an arsenic ion as a target metal element. Also, this invention is regarding methods and systems that efficiently and selectively remove or recover arsenic ion from arsenic ion solution that is dissolving arsenic ion.

BACKGROUND ART

Arsenic, which element symbol is As, is one of the fifteenth elements group and is broadly distributed in earth crust. Also, it is exposed as elemental substances in nature by volcanic activity, or it is artificially appeared on earth surface by mining of ores or fossil fuels. Since seawater contains 2 ppb arsenic, plankton and sea alga introduce arsenic from seawater and accumulate arsenic in themselves. Since arsenic is also accumulated in fish and shellfish that eat them, arsenic is introduced into our human body. Meanwhile, arsenic is toxic or harmful substance as typified by the arsenic milk incidents. It is said that a lethal dose of inorganic arsenic is approximately 2 mg per kilogram of human body weight, that is, 2 ppm. In addition, it is said that even an uptake of an ultratrace amount of arsenic less than the above amount causes symptom like a vomit or a stomachache or a diarrhea, etc., a hepatic function disorder or a paresis, etc. and that a chronic uptake causes a tumorigenicity or a nervous disorder. Accordingly, since an interfusion of arsenic ion into water is hazardous to life, arsenic is requested to be eliminated from food and drinking water that we take in.

In many communities, arsenic ion is detected at dangerous levels in public drinking water supplies even though arsenic is eliminated by treating water in a drinking water treatment plant. High arsenic concentrations in the drinking water have been recently reported from USA, China, Chile, Bangladesh, Taiwan, Mexico, Argentina, Poland, Canada, Hungary, and India, also Japan. In water, the most common valence states of arsenic are As(V), or an arsenate, which is more prevalent in aerobic surface waters, and As(III), or an arsenite, which is more likely to occur in anaerobic ground waters. In the pH range of 4 to 10, the predominant As (III) compound is neutral in charge, while the As (V) species are negatively charged.

A various kinds of methods to detect arsenic have been developed as follows. For example, there are High level analysis (X. Peng, G. S. Chen, Chin. J. Anal. Chem. 31 (2003) 38 and H. Matsunaga, C. Kanno, T. M. Suzuki, Talanta 66 (2005) 1287), Raman and Infrared spectroscopy C. Ludwig, H. J. Gotze, M. Dolny, Spectrochim. Acta Part A 56 (2000) 547 and C. Ludwig, M. Dolny, H. J. Gotze, Spectrochim. Acta Part A 53 (1997) 2363), ICP mass spectrometry V. Dufailly, L. Noel, T. Guerin, Anal. Chim. Acta 611 (2008) 134), Electrochemical analysis (R. Piech, W. W. Kubiak, J. Electroanal. Chem. 599 (2007) 59), Chemiluminescence analysis (C. Lomonte, M. Currell, M. J. S. Richard, Anal. Chim. Acta 583 (2007) 72), Atomic absorption analysis (J. Michon, V. Deluchat, R. A. Shukry, C. Dagot, J. C. Bollinger, Talanta 71 (2007) 47 and C. G. Bruhn, C. J. Bustos, K. L. Saez, J. Y. Neira, S. E. Alvarez, Talanta 71 (2007) 81), Atomic fluorescence analysis (X. Li, Y. Su, K. Xu, Talanta 72 (2007 1728)), and Chromatography (A. L. Lindberg, W. Goessler, M. Grander, B. Nermell, M. Vahter, Toxicol. Lett. 168 (2007) 310 and Y. C. Yip, H. S. Chu, C. F. Yuen, W. C. Sham, J. AOAC Int. 90 (2007) 284). Though these methods are certainly valuable and have individual advantages, it cannot be denied that they have some demerits. For example, though Zhu et al. disclose that a detection limit of $As^{3+}$ in Atomic absorption analysis of hydride evolution is 0.04 ngl-1 in the detection of As using a dielectric-barrier discharge vaporizer (Z. L. Zhu, J. Liu, S. H. Zhang, Anal. Chim. Acta 607 (2008) 136), there is fear that this method may be influenced a great deal by temperature. Also, Vincent et al. disclose a detection of As by a collision cell technology ICP-MS system. (D. Vincent, N. Laurent, G. Thierry, Anal. Chim. Acta 611 (2008) 134.) This method is high sensitivity, but multi atomic interference formation is found in the collision cell. Though Heitland et al. disclose a high-speed detection of As in urine by High-performance liquid chromatograph (HPLC) ICP/MS (P. Heitland, H. D. Koster, J. Anal. Toxicol. 32 (2008) 308), this method is expensive, in addition, organic solvent used is a large quantity and toxic. Though Matsunaga et al. newly developed a detection method by bare eye of a small amount of arsenic in water-soluble sample, this method needs advanced conditions that are adequately controlled. Furthermore, a detection limit of As by this method is $1 \times 10^{-6}$ mol $dm^{-3}$ and the reaction is very slow.

A condensation method, a catalytic method and an adsorption method are known as methods for removing arsenic ion. As the condensation method, it is known that arsenic ion could be removed by an oxidation agglomeration using iron salts or polyaluminum chloride (PAC) (general expression: $[Al_2(OH)nCl6-n]m$ (here, 1<n<5, m<10)), as shown in Japanese Patent Publication H07-088482. It shows that As concentration could be reduced to 0.0001 ppm, which satisfies a value less than 0.001 ppm that is an effluent standard adopted in 1993 in Japan. As the catalytic method, Japanese Patent Publication H09-327694 shows that arsenic ion is reduced and removed by hydrogen aeration using catalysts supporting rhodium to alumina (rhodium content 5 weight %, made by Aldrich Inc.) as a catalyst. As the adsorption method, the methods shown in Japanese Patent Publication 2000-176441, Japanese Patent Publication 2005-000747, Japanese Patent Publication 2000-024647, Japanese Patent Publication 2005-046728 and Japanese Patent Publication H10-137504 are known. Japanese Patent Publication 2000-176441 shows that arsenic ion concentration could be reduced less than 4000 μmol/L by using a mesostructure material of zirconium oxide system {the pore diameter D=20 to 50 nm, the contained amount of hexadecyltrimethylammoniumbromide (HTAB) was 39 wt %, and the cross-sectional diameter of HTAB is 30 to 40 nm.} that contained sulfate ion as an adsorbent. Japanese Patent Publication 2005-000747 shows that As concentration of the solution filtrated using a filter consisted of a chelate fiber immobilizing N-methyl-D-glucamine to a fibrous cellulose powder (Chelest fiber is provided by Chelest corporation) was 0.1 ppm or less. Japanese Patent Publication 2000-024647 shows that As concentration could be 8 ppm in the example using the material supporting 50 mass % to 60 mass % oxide or hydroxide of rare-earth metal to γ-alumina carrier (the average pore diameter is 119 nm, the pore volume is 0.713 cm3/g, the surface area is 240 m2/g, and the occupied ratio of 90 to 200 nm pores to the total volume is 88%) as an adsorbent. Patent Publication 2005-046728 shows that As concentration could be 8 ppm in the case of using an aminopropyl group modified magnetic-particle as an adsorbent. Japanese Patent Publication H10-137504 shows that As concentration could be reduced till $9 \times 10^{-7}$ mol/L by using a granular impregnation resin supporting 8 g bis(2-ethylhexyl) ammonium-bis(2-ethylhexyl)dithiocarbamate to 20 g polyacrylic acid ester resin.

SUMMARY OF THE INVENTION

Problems to be Resolved by the Invention

As mentioned above, to decrease arsenic ion concentration wherever possible by removing harmful arsenic ion from daily life water such as a drinking water in the environment should be achieved at all rates to protect human life. However, Technologies and methods to reduce the arsenic concentration in the solution to ppb-ppt levels of ultra trace concentration have not been found before now. Also, since it takes a long time to reduce the arsenic concentration in the drinking water to the low level with the traditional technology, the productivity is low and the cost can not be reduced. Furthermore, since special facilities and equipments are needed to reduce the arsenic concentration, they become factors of cost rises. To add acid or alkali in the solution to reduce the arsenic concentration causes a problem that the posttreatment (for example, removal or detoxifying) of the additives must be carried out in the next process, even though the arsenic concentration is reduced. Also, since the method to accelerate a reaction by heating needs large heating equipments and cooling system, the energy consumption and total cost to recover arsenic increase, even though the arsenic concentration is reduced.

Means of Solving the Problems

This invention is regarding a nanostructure material supporting an arsenic ion adsorption compound that can selectively and preferentially adsorb (or "extract" or "combine" may be used instead) arsenic $\{As(V)\}$ ion and this invention provides a system and a method to extract arsenic ion from an arsenic ion solution, which adsorb arsenic ion in the aqueous solution using the nanostructure material. Furthermore, this invention provides materials and methods to detect ppm-ppb-ppt levels of trace of arsenic ion in the solution. The brief summary of this invention is as follows.

(1) This invention is a nanostructure material supporting an arsenic ion adsorption compound, wherein the arsenic ion adsorption compound can adsorb arsenic ion from a solution (arsenic ion solution) dissolving arsenic $\{As(V)\}$ ion that is a target element, and the arsenic ion adsorbed can be eluted from the compound. The nanostructure material is a titania nanotube, a zinc oxide nanorod or an alumina nanorod (or mesoporous alumina).

(2) The titania nanotube is prepared by adding an ethanol dissolving a surfactant F108 to a mixed solution of a titanyl sulfate $(TiOSO_4)$, an ethanol and a sulfuric acid aqueous solution. The zinc oxide nanorod is prepared by adding a surfactant cetyltrimethyl ammonium bromide (CTAB) to a zinc chloride (ZnCl2) aqueous solution. The alumina nanorod is prepared by adding a surfactant CTAB to an aluminum nitrate aqueous solution.

(3) The arsenic ion adsorption compound is an ammonium molybdate. The ammonium molybdate is modified (or supported) on the nanostructure material (the titania nanotube, the zinc oxide nanorod, the alumina nanorod) by mixing the ammonium molybdate with the nanostructure material obtained after the titania nanotube, the zinc oxide nanorod or the alumina nanorod is treated by a surfactant, in the aqueous solution containing the ammonium molybdate. The surfactant is a dilauryl dimethyl ammonium bromide (DDAB).

(4) This invention is also a detection method of As ion concentration in the solution. Namely, after the above nanostructure material supporting the arsenic ion adsorption compound is put in an acid aqueous solution including As, and the solution is stirred, the solution is filtrated and the nanostructure is recovered and dried. Spectroscopic characteristics of the nanostructure material and the solution are measured. This invention is also a removal method of As ion in the solution. The nanostructure material adsorbing arsenic ion is put into the acid aqueous solution including arsenic ion, and the solution is stirred. Next, the nanostructure material is separated and removed from the solution. As a result, As-free aqueous solution can be obtained.

(5) This invention is also a recovery method of the nanostructure material supporting the arsenic ion adsorption compound, which is adsorbing As ion, that is used in the detection method or the removal method of arsenic ion in (4). The nanostructure material, which is adsorbing As ion, are put into an alkali solution, and the solution is stirred. As ion adsorbed by the nanostructure material is eluted into the alkali solution. This invention is also a detection method of As ion concentration in the solution or a removal method of As ion from the solution, using the nanostructure material recovered by the above methods.

(6) This invention is a mesoporous alumina supporting an arsenic ion adsorption compound, wherein the arsenic ion adsorption compound can adsorb arsenic ion from a solution (arsenic ion solution) dissolving arsenic $\{As(V)\}$ ion of a target element, and the arsenic ion adsorbed can be eluted from the compound. The mesoporous alumina is made with an aluminum nitrate and a surfactant. The surfactant is a camphorsulfonic acid (CSA) or a surfactant cetyltrimethyl ammonium bromide (CTAB). Or the mesoporous alumina is made by a hydrolysis of an aluminum isopropoxide $(C_9H_{21}AlO_3)$.

(7) The arsenic ion adsorption compound is the compound that can selectively and preferentially adsorb arsenic $\{As(V)\}$ ion of target element. It is a heteropoly acid. The heteropoly acid is an ammonium molybdate. Furthermore, the ammonium molybdate is supported by the mesoporous alumina by mixing a solid alumina, which is obtained after reacting the surfactant to the mesoporous alumina, in the solution including the ammonium molybdate. The temperature at which the ammonium molybdate supported by the mesoporous alumina adsorbs arsenic ion is room temperature. When the ammonium molybdate supported by the mesoporous alumina adsorbs arsenic ion by contacting with the arsenic ion solution, a pretreatment and/or a posttreatment such as a pH adjustment, etc. is not carried out.

(8) A concentration of the arsenic ion adsorbed is determined by a color using an ascorbic acid when the ammonium molybdate supported by the mesoporous alumina adsorbs arsenic ion by contacting with the arsenic ion solution. In addition, this invention is a detection method of the arsenic ion concentration in the arsenic ion solution using the above measure.

(9) This invention is a arsenic collector that collects arsenic (As) from the arsenic ion solution using the mesoporous alumina supporting the arsenic ion adsorption compound. Or, this invention is a filter to remove arsenic using the mesoporous alumina supporting the arsenic ion adsorption compound. Or, this invention is an arsenic adsorbent using the mesoporous alumina supporting the arsenic ion adsorption compound.

(10) This invention is an arsenic ion removal system, which can remove arsenic ion from the arsenic ion solution such as a natural water, a ditch before clarification, an industrial wastewater, a living drainage and other solution using the mesoporous alumina supporting the arsenic ion adsorption compound, and can make the solution after the removal of arsenic ion available to a drinking water, a daily life water, an agricultural water and a industrial water.

(11) This invention is an arsenic ion removal equipment, which can remove arsenic ion by pouring the arsenic ion solution into the pod holding the mesoporous alumina supporting the arsenic ion adsorption compound, or by adding the mesoporous alumina supporting the arsenic ion adsorption compound in the pod holding the arsenic ion solution. Furthermore, the arsenic ion concentration in the arsenic ion solution is reduced less than a constant concentration such as the tolerance limit of arsenic or the limit concentration for adsorbing arsenic by multiple contacts between the arsenic ion solution and the mesoporous alumina supporting the arsenic ion adsorption compound by connecting plural of the said equipments serially

(12) This invention is an arsenic ion recovery method using the mesoporous alumina supporting the arsenic ion adsorption compound, which contains a process in which the mesoporous alumina supports the arsenic ion adsorption compound, a process in which arsenic ion is selectively adsorbed by the arsenic ion adsorption compound supported by the mesoporous alumina, by contacting the mesoporous alumina supporting the arsenic ion adsorption compound with the arsenic ion solution, and a process in which arsenic ion is eluted from the arsenic ion adsorption compound adsorbing arsenic ion.

(13) This invention is an arsenic ion recovery method, which contains the following in addition to (12). The mesoporous alumina supporting the arsenic ion adsorption compound can be reused. The arsenic ion adsorption compound can selectively adsorb arsenic ion, the arsenic ion adsorption compound is a heteropoly acid, and the heteropoly acid is ammonium molybdate.

(14) This invention is an arsenic ion recovery method, which contains the following in addition to (13). The ammonium molybdate is supported by the mesoporous alumina by mixing the solid alumina, which is obtained by reacting the mesoporous alumina to a surfactant, in the solution containing the ammonium molybdate. The temperature to adsorb arsenic ion by contacting between the mesoporous alumina supporting the arsenic ion adsorption compound and the arsenic ion solution is a room temperature. When the ammonium molybdate supported by the mesoporous alumina adsorbs arsenic ion by contacting with the arsenic ion solution, a pretreatment and/or a posttreatment such as pH adjustment is not carried out. A concentration of the arsenic ion adsorbed is determined by a color using an ascorbic acid when the ammonium molybdate supported by the mesoporous alumina adsorbs arsenic ion by contacting with the arsenic ion solution.

Advantageous Effect of the Invention

The nanostructure materials (a titania nanotube, a zinc oxide nanorod or an alumina nanorod (mesoporous alumina)) have a strong structural molecular frame, and the outer and inner surfaces of them have large scale of porous structures. Many arsenic ion adsorption compounds are supported on the surfaces of the porous structures having large specific surface area. Accordingly, since the adsorption efficiency of arsenic ion by the arsenic ion adsorption compound is very high and the removal efficiency of arsenic ion from the arsenic ion solution is very high, the adsorption and removal of arsenic ion in the arsenic ion solution can be rapidly carried out. Furthermore, since the nanostructure materials have many adsorbed sites and the individual nanosize site woks to adsorb arsenic ion, it can remove not only ppm level of arsenic but also ppb-ppt levels of ultra trace of arsenic ion. Especially if the arsenic ion adsorption compound is a heteropoly acid such as ammonium molybdate, it can selectively, preferably and much efficiently adsorb arsenic ion compared to other cations or anions.

Since ammonium molybdate is efficiently supported on the porous surface having a large surface area by reacting ammonium molybdate after treating the nanostructure material with a surfactant, arsenic ion is adsorbed efficiently from ultra trace level to high concentration level to increase the adsorbed sites of arsenic ion. Furthermore, since the mesoporous alumina supporting such ammonium molybdate can adsorb arsenic ion rapidly and heavily at room temperature without heating even though pretreatment and/or posttreatment such as pH control in the arsenic ion solution are carried out, especial heating measures are not needed and energy consumption doe not increase. Accordingly, our system is economical. For example, in a clarification system of water, the mesoporous alumina supporting ammonium molybdate may be only put into the unpurified water, and then after arsenic ion is adsorbed by the mesoporous alumina, the mesoporous alumina supporting ammonium molybdate, which is adsorbing arsenic ion, may be only removed from the solution. In addition, by multi stage arsenic ion removal system using plural of arsenic removal equipments of the present invention, arsenic ion can be removed rapidly and heavily from the unpurified water. As a result, we can supply arsenic-free solution (that is, a drinking water). Also, we can detect the arsenic ion concentration in the solution at low level (ppm-ppb-ppt level), and in a short time (several minutes to several ten minutes). Furthermore, since the nanostructure material supporting arsenic ion adsorption compound of the present invention can separate arsenic ion after absorbing arsenic ion, it can be reused. Accordingly, the running cost of the arsenic detection and arsenic removal can be reduced dramatically. Well, the nanostructure supporting arsenic ion adsorption compound of the present invention may be named "element arsenic (As) (ion) adsorption", that is, "EAA".

BRIEF DESCRIPTION OF THE DRAWINGS

FIG. 5 shows a scanning electron micrograph of the zinc oxide nanorod in Example 1.

FIG. 6 shows a photograph that expresses the alumina nanorod in Example 1.

FIG. 26 is a table that shows the data measured by ICP-OES in the arsenic ion concentration in the solution.

FIG. 27 is a table that shows an arsenic ion concentration and a removal efficiency of arsenic before and after the alumina-captors in the natural water were processed.

EMBODIMENTS FOR CARRYING OUT THE INVENTION

Figure 1:
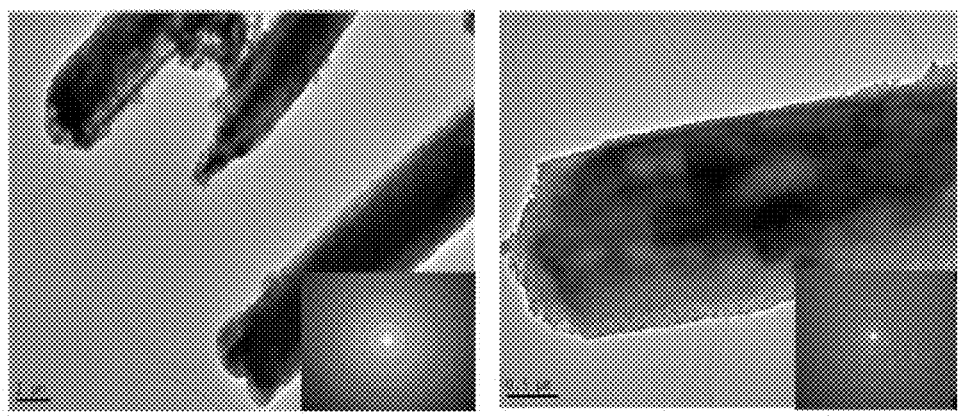
FIG. 1 shows a high-resolution transmission electron micrograph and an electron diffraction pattern that express $TiO_2$ nanotube in Example 1.
Figure 2:
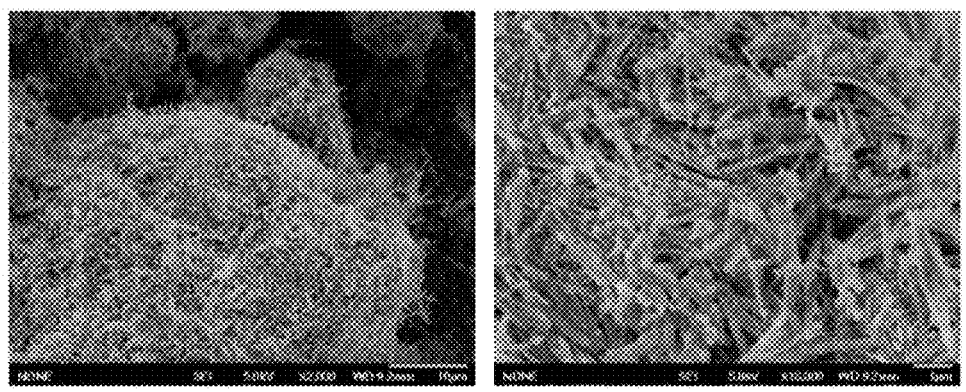
FIG. 2 shows a scanning electron micrograph of $TiO_2$ nanotube in Example 1.
Figure 3:
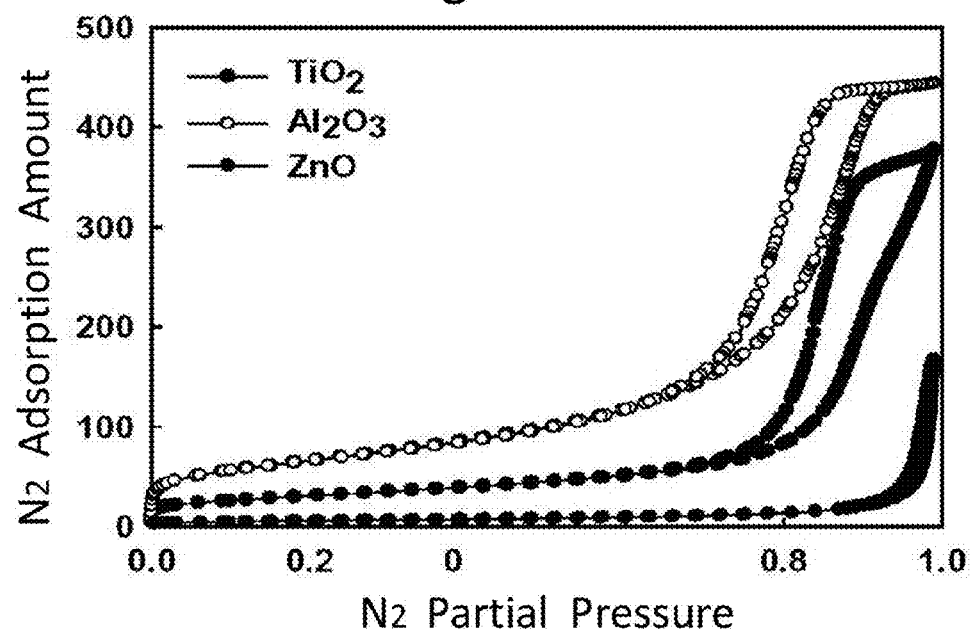
FIG. 3 is a graph that shows a nitrogen adsorption and desorption isotherm of $TiO_2$ nanotube, the alumina nanorod and the zinc oxide nanorod at 70K in Example 1.
Figure 4:
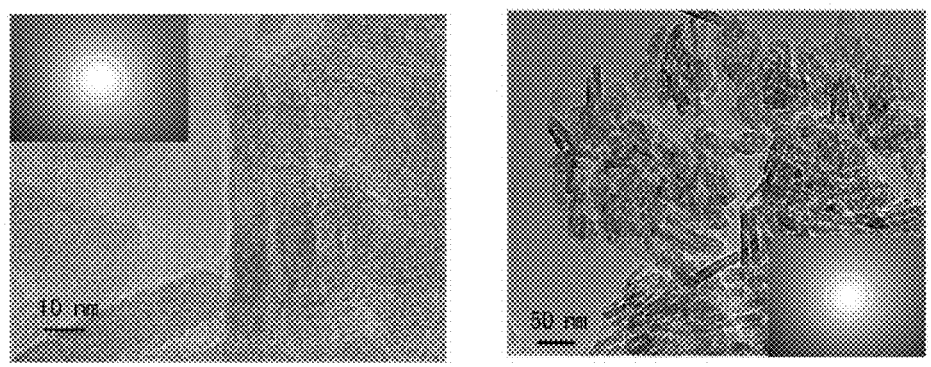
FIG. 4 is shows a high-resolution transmission electron micrograph that expresses the alumina nanorod in Example 1.
Figure 7:
FIG. 7 shows a photograph of the element of As adsorption used for the characterization in Example 3.

This invention provides a detection technique of arsenic ion and a removal technique of arsenic ion using an arsenic ion adsorption compound having a high selective and optical detective function. Furthermore, this invention provides a clarification system removing arsenic ion from a daily life water such as a drinking water, a natural water and an agricultural water using the removal technique of arsenic ion. The feature of the technique is that a surface state of nanosize arranging at atomic level the mesoporous material that has nanostructure consisted of heterogeneous atomics is utilized. This invention can remove ppb-ppt level of trace of arsenic ion and does not affect the environment and can be used at low cost. From these points, this invention is very excellent as a method to extract arsenic from waste and effluent containing various kations and anions.

We explain some embodiments of this invention in detail as follows. Element of As adsorption (or arsenic (As) adsorption device) of the present invention contains the nanostructure (or nanocarrier) material supporting the arsenic ion adsorption compound that changes color by adsorbing arsenic ion. The arsenic ion adsorption compound may be named "arsenic (As) receptor". The nanostructure material is a crystalline body that is basically below one micron meter in any of the length, the diameter or the thickness of the shell (if it has a shell such as nanotube). Also, it is used as a concept containing not only a nanotube and a nanorod, but also other shapes such as a corn, a sphere. For example, it is a titania nanotube, a zinc oxide nanorod or an alumina nanorod. In some cases, this invention is available in the crystalline body more than one micron meter in length, in diameter, or in thickness of the shell. Though an element of As adsorption (or As adsorption device) of the present invention contains the arsenic ion adsorption compound that changes color by adsorbing As ion, and the nanostructure material supporting the said compound, since it is very important to measure spectroscopic characteristics of the element of As adsorption that is adsorbing As, As adsorption device does not preferably have the disturbance factors of the measurement wherever possible to measure accurately. So, the arsenic ion adsorption compound and the nanostructure material are preferably colorless.

Also, since a nanostructure material interfering with As has the potential to disturb the As adsorption of the As ion adsorption compound, silica ($SiO_2$), ferric oxide ($Fe_2O_3$), chrome oxide ($CrO_2$), etc. are not used preferably as the nanostructure material. In short, it is preferable that As adsorption device of the present invention is colorless and has the structure supported by the colorless nanostructure material that does not interfere with $As^{5+}$ and does not change color. Though ammonium molybdate is shown as an instance of As ion adsorption compound in the below examples, in addition to this, we can use some materials to be supported and combined by the nanostructure material such as the titania nanotube supporting As ion adsorption compound like the above. Moreover, if the colorless nanostructure materials do not interfere with As, they can be used as well as the above materials.

We explain an element of As adsorption using a titania nanotube, an alumina nanorod, or a zinc oxide nanorod in FIG. 1 to FIG. 9. To adsorb arsenic ion ($As^{5+}$) in the solution to the element of As adsorption (hereinafter called "EAA"), temperature, pH, and stirring (holding) time in the target solution and input amount of EAA should be desirably selected as below. The solution is desirably acid, the lower limitation of pH value is 0.5, preferably 1.0 or more preferably 2.0, and the above limit is 6.0, preferably 5.0, or more preferably 4.5. If the solution is neutral or alkali, arsenic ion ($As^{5+}$) may not be adsorbed. The temperature of the solution needs room temperature or higher temperature. Especially the temperature at which As ion adsorption compound does not metamorphose is desirable, concretely, it is desirable that it is 30° C. to 50° C., preferably 35° C. to 45° C.

If the temperature of the solution is below room temperature, very long adsorption time of arsenic ion ($As^{5+}$) may be needed. In such case, arsenic ion may not be adsorbed sufficiently in the short time less than one hour. It is desirable that the input amount of EAA put into such the solution is $6\times10^{-9}$ to $2\times10^{-5}$ mol/L, preferably $6.7\times10^{-9}$ to $1.4\times10^{-5}$ mol/L. By putting such input of EAA and stirring moderately, low concentration of arsenic ion ($As^{5+}$) can be adsorbed. Though too much input of EAA do not cause large problem regarding the arsenic ion ($As^{5+}$) adsorption, such excessive input should be avoided because EAA is used wastefully. It is desirable that the stirring (holding) time is less than one hour, preferably 15 minutes to 45 minutes. If the time is too short, trace of arsenic ion ($As^{5+}$) may not be adsorbed. However, even though the time is too much, the adsorption amount of arsenic ion ($As^{5+}$) won't increase.

In analysis of ultraviolet-visible spectrophotometry (UV-Vis spectrophotometry), it is adequate to use the wavelength of maximum absorption ($\lambda$ max). That is, it is 853 nm for a titania oxide supporting ammonium molybdate $\{(NH_4)_6Mo_7O_{24}-TiO_2\}$, 853 nm for an alumina oxide supporting ammonium molybdate $\{(NH_4)_6Mo_7O_{24}-Al_2O_3\}$, or 812 nm for a zinc oxide supporting ammonium molybdate $\{(NH_4)_6Mo_7O_{24}-ZnO\}$. Since the wavelength of maximum absorption ($\lambda$ max) varies according to the structure of EAA, it is determined by the data such as FIG. 8.

If EAA adsorbing As as the above mentioned is put into an alkali ion solution and stirred, arsenic ion ($As^{5+}$) adsorbed to EAA is eluted into the solution. Since the adsorption capability of EAA is recovered by this treatment, EAA can be reused. The alkali ion solution is an aqueous sodium hydroxide (NaOH). 0.5 mol/L of the aqueous sodium hydroxide can elute arsenic ion ($As^{5+}$) from EAA without changing the binding state between the arsenic ion adsorption compound and the nanostructure material.

The adsorption capability (AC) of arsenic ion ($As^{5+}$) of EAA recovered by the forementioned method is shown in Table 1. Since the adsorption capability of arsenic ion ($As^{5+}$) of EAA recovered is inhibited by ions in the solution containing cations and anions, it is considered that the adsorption capability decreases compared to the degree of separation (DS) of arsenic ion ($As^{5+}$). Efficiency of the recovery (E %) is calculated as below. The adsorption capability of arsenic ion ($As^{5+}$) of EAA was obtained from data of UV-Vis spectrophotometry measured after EAA adsorbed arsenic ion ($As^{5+}$), and the initial value (A0) was obtained after initial EAA adsorbed arsenic ion ($As^{5+}$), first recovery value (A1) was obtained after EAA recovered by once recovery adsorbed arsenic ion ($As^{5+}$), fifth recovery value (A5) was obtained after EAA recovered by five times recovery adsorbed arsenic ion ($As^{5+}$). And then, the adsorption capability of arsenic ion ($As^{5+}$) of EAA (E %) is calculated by $E=(A_5/Ao)\times100(\%)$. Though the adsorption capability of arsenic ion ($As^{5+}$) of EAA decreases gradually according to the recovery times, the adsorption capability of the EAA of 10 times recovery is 70% or more. As a result, it is proved that our EAA can be used repeatedly. It is considered that the adsorption capability of EAA and the recovery times can be improved by the optimization of the heating conditions. Also, from the result, since our EAA has the excellent adsorption capability of arsenic ion ($As^{5+}$), clean water can be obtained by removing arsenic ion from the solution containing arsenic ion.

TABLE 1

|     | Once Recovery | | 5 times Recovery | | 10 times Recovery | |
| --- | --- | --- | --- | --- | --- | --- |
| EAA | DS | AC | DS | AC | DS | AC |
| 1 | 97% | 96% | 84% | 81% | 73% | 70% |
| 2 | 98% | 97% | 87% | 82% | 76% | 72% |
| 3 | 96% | 95% | 82% | 78% | 74% | 70% |

1; $(NH_4)_6Mo_7O_{24}-TiO_2$ (Titania nanotube supporting Ammonium Molybdate)
2; $(NH_4)_6Mo_7O_{24}-Al_2O_2$ (Almina supporting Ammonium Molybdate)
3; $(NH_4)_6Mo_7O_{24}-ZnO$ (Zinc oxide supporting Ammonium Molybdate)

Example 1

Synthesis Process of Titania Nanotube

This example exemplifies a synthesis process of a titania nanotube of one of the nanostructure materials. 8 g titanyl sulfate, 10 g ethanol and 5 g $H_2O/H2SO_4$ (1 Mol) were mixed and a milky solution was obtained. Next, after 4 g F108 surfactant was added to 5 g ethanol, the ethanol was rapidly added to the milky solution. The mass ratio of $TiOSO_4$:F108:$H_2O/H_2SO_4$ was 1:0.5:0.6. After the ethanol was decompressed and removed with heating at 40° C. to 50° C. in the rotary evaporator, a gel-like solid was formed within 5 minutes. Other organic constituent was removed by calcining for 8 hours. The titania nanotube obtained has the structure shown in FIG. 1, FIG. 2 and FIG. 3. Other structural parameters are shown in Table 3. A size of the titania nanotube obtained is shown in Table 2.

<Synthesis Process of Alumina Nanorod>

Synthesis process of an alumina nanorod structure can be easily obtained by the following procedure. 8 g precursor aluminum nitrate $\{Al(NO3)3\}$ was dissolved in 20 ml water. After 4 g surfactant cetyltrimethylammonium bromide (CTAB) was dissolved in 10 ml water, they were mixed and stirred for one hour. Next, the solution was stirred for 30 minutes and adjusted to pH10 by adding a concentrated ammonia.

After the reactant mixture was transferred to a Teflon™-lined stainless-steel pressure steam sterilizer and sealed, it was heated for 24 hours in the oven kept at 150° C. The sterilizer was naturally cooled to room temperature. The mixture obtained was separated by a centrifugation, and the sediment was sufficiently washed 3 times with distilled water and ethanol, and was calcined for 8 hours at 500° C. The mass ratio of $Al(NO_3)_3$:CTAB:$H_2O$ was 1:0.5:3.75. The characteristics are shown in Table 3, and the size is written in Table 2.

<Synthesis Process of Zinc Oxide Nanorod>

Synthesis process of a zinc oxide nanorod can be easily obtained by the following procedure. 1.36 g precursor zinc chloride ($ZnCl_2$) was dissolved in 30 ml water. After 0.68 g surfactant cetyltrimethylammonium bromide (CTAB) was dissolved in 20 ml water, they were mixed and stirred for one hour. Next, the solution was stirred for 30 minutes and adjusted to pH10 by adding a concentrated ammonia. After the reactant mixture was transferred to a Teflon™-lined stainless-steel pressure steam sterilizer and sealed, it was heated for 16 hours in the oven kept at 160° C. The sterilizer was naturally cooled to room temperature. The mixture obtained was separated by a centrifugation, and the sediment was sufficiently washed 3 times with distilled water and ethanol, and was calcined for 8 hours at 500° C. The mass ratio of $ZnCl_2$:CTAB:$H_2O$ was 1:0.5:36.76.

The characteristics are shown in Table 3, and the size is written in Table 2.

TABLE 2

| Nanostructure | Length (nm) | | | Gauge (nm) | | |
|---|---|---|---|---|---|---|
| | Maximum | Average | Minimum | Maximum | Average | Minimum |
| Titania Nanotube | 12750 | 10120 | 8740 | 2230 | 2030 | 1030 |
| Alumina Nanorod | 61 | 57 | 50 | 15 | 13 | 10 |
| Zinc Oxide Nanorod | 500 | 450 | 400 | 100 | 85 | 75 |

TABLE 3

| | Structural Parameter | | |
|---|---|---|---|
| Nanostructure | $S_{BET}$ $m^2/g$ | Dp nm | Vp $cm^3/g$ |
| Titania Nanotube | 107.9 | 9.3 | 0.58 |
| Almina Nanorod | 211.0 | 8.02 | 0.69 |
| Zinc Oxide Nanorod | 19.7 | 34.4 | 0.25 |

$S_{BET}$; BET Specific Surface Area
Dp; Pore Diameter,
Vp; Pore Volume

Example 2

This example exemplifies a method to obtain EAA by an ammonium molybdate supported by the titania nanotube prepared in the said Example 1.

(Step 1)

1 mg titania and 0.3 mg surfactant dilauryl dimethyl ammonium bromide (DDAB) {$[CH_3(CH_2)_{11}]_2(CH_3)_2NBr$} were mixed and stirred, and they were sucked and exhausted for 30 minutes at 35° C. by a rotary evaporator. Next, they were vacuumed and dried at 45° C. by the vacuum pump of the rotary evaporator. The solid obtained was washed, and dried at normal pressures and at 45° C.

(Step 2)

The solid obtained was mixed in the solution in which 0.3 mg $(NH_4)_6Mo_7O_{24}24H_2O$ was mixed in 50 ml water, and was stirred for 12 hours.

(Step 3)

The mixed solution was filtrated. The solid obtained was washed and was vacuumed and dried at 55° C. EAA supporting $(NH_4)_6Mo_7O_{24}$ on the surface of the titania is prepared. The structure shown in FIG. 4 and FIG. 5, and the structural parameters are shown in Table 4. The alumina nanorod and the zinc oxide nanorod can be prepared with the same procedure as the above, that is, their sensors can be obtained by exchanging the titania in Step 1 for an alumina and an zinc oxide. The size of EAA is nearly equal to that of the said nanostructure material.

TABLE 4

| | EAA | Structural Parameter | | |
|---|---|---|---|---|
| | | $S_{BET}$ $m^2/g$ | Dp nm | Vp $cm^3/g$ |
| 1 | $TiO_2$—$(NH_4)_6Mo_7O_{24}$ | 34.8 | 4.02 | 0.16 |
| 2 | $Al_2O_3$—$(NH_4)_6Mo_7O_{24}$ | 135.4 | 5.28 | 0.41 |
| 3 | $ZnO$—$(NH_4)_6Mo_7O_{24}$ | 2.7 | 2.1 | 0.03 |

$S_{BET}$; BET Specific Surface Area
Dp; Pore Diameter,
Vp; Pore Volume

Example 3

This example exemplifies a detection of arsenic concentration in the solution using EAA obtained in Example 2. Twelve kinds of detective solutions shown in Table 5 were respectively mixed with a sulfuric acid aqueous solution as pH adjuster and three kinds of EAA. These mixed solutions were stirred for 25 minutes at 40° C. Next, EAA was recovered and dried after a filtration of the solution. (See FIG. 6) FIG. 8 and Table 6 show Characterization of these materials obtained by using ultraviolet, visible, and far-red spectrophotometer (SolidSpec-3700DUV made by Shimadzu corporation). Ascorbic acid was mixed to change blue color by changing hexavalent molybdenum {Mo(VI)} of As ion adsorption compound {$(NH_4)_3[As(Mo_3O_{10})_4]$ complex} to pentavalent molybdenum {Mo(V)} of {$(NH_4)_7[As(Mo_3O_{10})_4]$ complex}.

Figure 8:
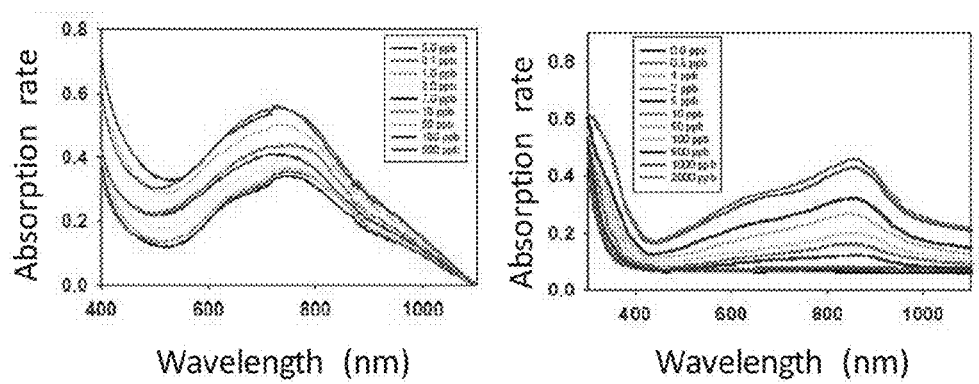
FIG. 8 is a graph that shows the results of the adsorption spectra of the titania and the alumina after As detection in Example 3.
Figure 9:
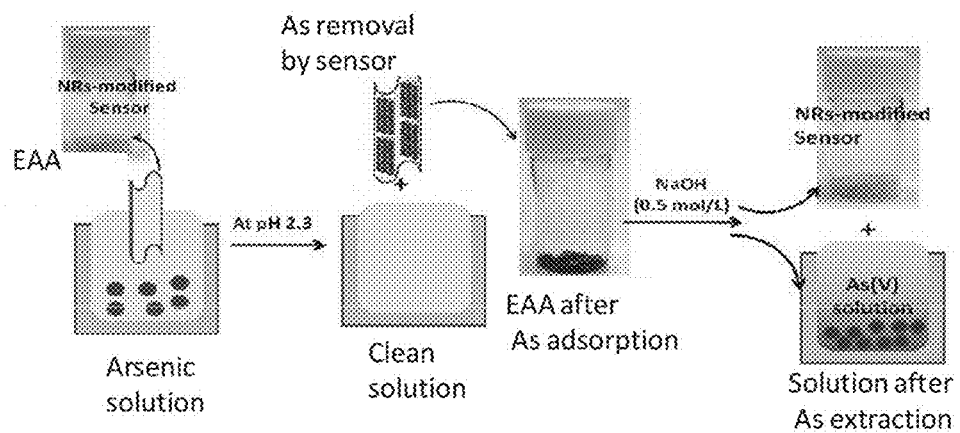
FIG. 9 is a diagrammatic illustration that shows a procedure to fabricate clean water by removing As from a polluted water using a material supporting the element of As adsorption.

There is a definite correlative relationship between ppb level of As ion concentration and absorption rate (abs.) by the characterization, as is clear from Table 5 and FIG. 8. From the correlative relationship, arsenic ion ($As^{5+}$) concentration in the solution can be identified. That is, arsenic ion ($As^{5+}$) concentration in the solution can be calculated by measuring the intensity of the specific wavelength of the above spectrophotometer. This proves that the nanostructure material supporting As ion adsorption compound, namely EAA (Element of As Adsorption) is useful as As ion sensor. Here, As concentration of the detected solution was adjusted by mixing dibasic sodium arsenate ($Na_2HAsO_4$). $1.34 \times 10^{-9}$ mol/L of dibasic sodium arsenate was mixed to obtain 0.1 ppb of As concentration. The pH value in the solution was adjusted within the range of 2-2.5 since a difference of 0.5 do not affect the As concentration.) If the pH value was out of the above range, furthermore it was adjusted to fall within the above range using $H_2SO_4$. 10 ml solution was prepared by 5 mg solid sensor and the solution {0.5 ml (H2SO4+9.5H2O)+2 ml ascorbic acid+1 ml (Na2HAsO4)} and water to detect arsenic ion ($As^{5+}$) concentration.

TABLE 5

| No. | Detected solution | | | Temp | Time | EAA | | Absorption Rate (abs.) | | |
|---|---|---|---|---|---|---|---|---|---|---|
| | Ascorbic Acid | As Concent. | pH | °C. | No. | 20 ml | EAA1 | EAA2 | EAA3 |
| 1 | 2 ml (0.01 mol/L) | 0 ppb | 2.3 | 40 | 1 | 20 mg | 0.335 | 0.065 | 0.120 |
| 2 | 2 ml (0.01 mol/L) | 0.1 ppb | " | " | 2 | " | 0.349 | — | 0.139 |
| 3 | 2 ml (0.01 mol/L) | 0.5 ppb | " | " | 3 | " | 0.355 | 0.074 | 0.160 |
| 4 | 2 ml (0.01 mol/L) | 1 ppb | " | " | 4 | " | 0.361 | 0.081 | 0.221 |
| 5 | 2 ml (0.01 mol/L) | 2 ppb | " | " | 5 | " | 0.384 | 0.087 | 0.334 |
| 6 | 2 ml (0.01 mol/L) | 7 ppb | " | " | 6 | " | 0.407 | 0.121 | 0.411 |
| 7 | 2 ml (0.01 mol/L) | 10 ppb | " | " | 7 | " | 0.433 | 0.161 | 0.537 |
| 8 | 2 ml (0.01 mol/L) | 50 ppb | " | " | 8 | " | 0.503 | 0.210 | 0.653 |
| 9 | 2 ml (0.01 mol/L) | 100 ppb | " | " | 9 | " | 0.556 | 0.265 | 0.765 |
| 10 | 2 ml (0.01 mol/L) | 500 ppb | " | " | 10 | " | 0.559 | 0.359 | 0.782 |
| 11 | 2 ml (0.01 mol/L) | 1000 ppb | " | " | 11 | " | — | 0.427 | — |
| 12 | 2 ml (0.01 mol/L) | 2000 ppb | " | " | 12 | " | — | 0.457 | — |

EAA1; $(NH_4)_6MO_7O_{24}$—$TiO_2$ λ max: 731
EAA2; $(NH_4)_6MO_7O_{24}$—$Al_2O_3$ λ max: 853
EAA3; $(NH_4)_6MO_7O_{24}$—ZnO λ max: 812

Example 4

This example exemplifies a recovery process of EAA (As was adsorbed. It may be called "EAA-As" below) used in Example 3. Arsenic (As) adsorbed to EAA can be separated by putting EAA-As in the alkali solution. Concretely, As could be eluted from EAA-As in the solution by putting EAA-As into 0.5 mol/L of NaOH solution. As a result, EAA could be recovered by separating and drying EAA from the solution. The EAA recovered may be called "EAAR" below. The adsorption capability of $As^{5+}$ of the EAAR was investigated under the conditions shown in No. 10 of Table 5. The result is written in column A of Table 6. As the recovery times increase, the adsorption capability of $As^{5+}$ decreases. However, it is proved that the EAA sensor is generally effective after the longitudinal detection and the recovery cycle.

In the case that EAAR is recovered using EAA or EAAR adsorbing As from the solution that contains the amount beyond the tolerance limit (TL) of the elements or organic materials such as shown in Table 7, it is considered that the EAAR may affect the measurement (characterization) of As adsorption Particularly, it is found that the heteropoly molybdenum formed in acid state by phosphate and silica anion may cause a significant problem in the measurement of As adsorption. To avoid such problem, a removal of phosphate and silica anion is requested. We used an anion-exchange resin (Dowex™ Marathon WBA) to separate perfectly the phosphate from As ion. That is, phosphate anion was perfectly removed after the sample containing 5 ppm phosphate anion passed the column of the anion-exchange resin. The silica can be separated by adding 0.1 mol/L of sodium fluoride (NaF) of masking agent. It is found that As adsorption capability is resistant to the silica anion within 10 ppm under 0.1 mol/L of sodium fluoride (NaF). It is confirmed that the existence of the other ions does not cause significant positive errors. It is desirable to use EAA with EAAR to cover the degradation of the As adsorption capability by EAAR in the case of EAA basis.

TABLE 6

| | Absorption Rate (abs.) | | | | | | Adsorption Capability (%) | | | | | |
|---|---|---|---|---|---|---|---|---|---|---|---|---|
| Recovery | EAAR1 | | EAAR2 | | EAAR3 | | EAAR1 | | EAAR2 | | EAAR3 | |
| Times | A | B | A | B | A | B | A | B | A | B | A | B |
| 0 | 0.559 | 0.559 | 0.359 | 0.359 | 0.782 | 0.782 | 100 | 100 | 100 | 100 | 100 | 100 |
| 1 | 0.542 | 0.536 | 0.351 | 0.348 | 0.750 | 0.742 | 97 | 96 | 98 | 97 | 96 | 95 |
| 2 | 0.519 | 0.519 | 0.344 | 0.341 | 0.727 | 0.719 | 93 | 93 | 96 | 95 | 93 | 92 |
| 3 | 0.497 | 0.491 | 0.337 | 0.326 | 0.703 | 0.688 | 89 | 88 | 94 | 91 | 90 | 88 |
| 4 | 0.480 | 0.469 | 0.323 | 0.308 | 0.672 | 0.641 | 86 | 84 | 90 | 86 | 86 | 82 |
| 5 | 0.469 | 0.452 | 0.312 | 0.294 | 0.641 | 0.609 | 84 | 81 | 87 | 82 | 82 | 78 |
| 6 | 0.452 | 0.441 | 0.301 | 0.287 | 0.624 | 0.594 | 81 | 79 | 84 | 80 | 80 | 76 |
| 7 | 0.441 | 0.424 | 0.290 | 0.280 | 0.609 | 0.578 | 79 | 76 | 81 | 78 | 78 | 74 |
| 8 | 0.424 | 0.413 | 0.283 | 0.272 | 0.594 | 0.563 | 76 | 74 | 79 | 76 | 76 | 72 |

TABLE 6-continued

| | Absorption Rate (abs.) | | | | | | Adsorption Capability (%) | | | | | |
|---|---|---|---|---|---|---|---|---|---|---|---|---|
| Recovery | EAAR1 | | EAAR2 | | EAAR3 | | EAAR1 | | EAAR2 | | EAAR3 | |
| Times | A | B | A | B | A | B | A | B | A | B | A | B |
| 9 | 0.413 | 0.402 | 0.265 | 0.265 | 0.586 | 0.555 | 74 | 72 | 77 | 74 | 75 | 71 |
| 10 | 0.408 | 0.391 | 0.262 | 0.258 | 0.578 | 0.547 | 73 | 70 | 76 | 72 | 74 | 70 |

Recovery Times 0 means an initial EAA
EAAR1; $(NH_4)_6MO_7O_{24}$—$TiO_2$ λ max: 731 nm
EAAR2; $(NH_4)_6MO_7O_{24}$—$Al_2O_3$ λ max: 853 nm
EAAR3; $(NH_4)_6MO_7O_{24}$—$ZnO$ λ max: 812 nm

TABLE 7

| Common electrolyte species (ppm) | | | | | | | | | | | |
|---|---|---|---|---|---|---|---|---|---|---|---|
| Cation | $NO_3^-$ | $F^-$ | $Cl^-$ | $SO_4^{2-}$ | $Br^-$ | $NO^{2-}$ | $CO_3^{2-}$ | $IO_3^-$ | $SO_3^{2-}$ | $SCN^-$ | $SiO_3^{2-}$ | $PO_4^{3-}$ |
| Tolerance limit | 55 | 37 | 50 | 20 | 20 | 30 | 30 | 15 | 20 | 18 | $10^a$ | $5^b$ |

| Surfactants and complexing agents (μM) | | | | | | | | | | |
|---|---|---|---|---|---|---|---|---|---|---|
| Cation | CTAB | TAAC | TEAC | DDAB | SDS | TX | Oxal. | Citr. | Tart. | Phth | Acet. |
| Tolerance limit | 40 | 40 | 45 | 35 | 20 | 50 | 55 | 50 | 60 | 65 | 45 |

| Foreign cations (ppm) | | | | | | | | |
|---|---|---|---|---|---|---|---|---|
| Metal ion | $Cr^{3+}$ | $Fe^{3+}$ | $Mg^{2+}$ | $Co^{2+}$ | $Ni^{2+}$ | $Mo^{8+}$ | $Zn^{2+}$ | $Ca^{2+}$ |
| Tolerance limit | 34 | 25 | 50 | 24 | 25 | 30 | 14 | 40 |
| Metal ion | $Sn^{2+}$ | $Pb^{2+}$ | $Bi^{3+}$ | $Hg^{2+}$ | $Cd^{2+}$ | $Al^{3+}$ | $Sb^{3+}$ | |
| Tolerance limit | 12 | 10 | 10 | 8 | 15 | 10 | 8 | |

Explanatory note
CTAC: (Cetyltrimethyl ammonium bromide)
DDAB: (Dilauryl dimethyl ammonium bromide)
TAAC: (Tetraamyl ammonium chloride)
TEAC: (Tetraethyl ammonium chloride)
SDS: (Sodium dodecyl sulfate)
TX: (Triton X-100)
Oxal.: (Oxalate)
Citr: (Citrate)
Tart.: (Tartrate)
Phth.: (Phthalate)
Acet.: (Acetate)
$^a$(with masking using sodium fluoride)
$^b$(with pretreatment using anion-exchange resin.)

Example 5

As shown in Example 3, EAA of this invention has a function to adsorb arsenic ion ($As^{5+}$) contained in the acid solution and can maintain the adsorption state till it contact with the alkali solution. By utilizing this function, EAA can remove arsenic ion ($As^{5+}$) contained in the aqueous solution and can be used to obtain clean water. 20 mg EAA was put into 20 ml solution, and arsenic ion ($As^{5+}$) contained in the solution was removed by adsorbed by the EAA. The concentration of arsenic ion ($As^{5+}$) contained in the solution was measured with ICP emission spectrophotometer before and after this treatment. The result is shown in Table 9. As shown in Table 9, we can make the clean water in which arsenic ion ($As^{5+}$) was removed. Moreover, it goes without saying that EAA used in the cleanup can recover using the method shown in the said Example 4. If EAAR is used in this Example, it is appropriate to use the more amount of EAAR than the amount of EAA by considering the degradation of the adsorption capability of arsenic ion ($As^{5+}$). To decrease the remaining amount of arsenic ion ($As^{5+}$) in the solution less than the value shown in Table 8, it is considered that the input amount of EAA may be increased more than that shown in Table 8. Furthermore, If EAA is used only to remove arsenic ion ($As^{5+}$), the colored materials, which is inappropriate to detect, can be used as EAA since colored EAA is also good.

TABLE 8

| As concentration (ppb) in the solution with ICP emission spectrophotometer before and after As extraction using EAA | | | | | | |
|---|---|---|---|---|---|---|
| EAA | | EAA1 | | EAA2 | | EAA3 |
| No. | Input | Before | After | Before | After | Before | After |
| 1 | 20 mg | 47.9 | 2.1 | 48.5 | 1.5 | 47.8 | 2.2 |
| 2 | 20 mg | 97.9 | 2.4 | 98.9 | 1.1 | 98.0 | 2.0 |
| 3 | 20 mg | 497.0 | 3.0 | 498.0 | 2.0 | 497.5 | 2.5 |
| 4 | 20 mg | 998.0 | 2.0 | 998.5 | 1.5 | 997.1 | 2.9 |
| 5 | 20 mg | 1980 | 20 | 1985 | 15 | 1980 | 20 |

EAA1; $(NH_4)_6MO_7O_{24}$—$TiO_2$ λ max: 731
EAA2; $(NH_4)_6MO_7O_{24}$—$Al_2O_3$ λ max: 853
EAA3; $(NH_4)_6MO_7O_{24}$—$ZnO$ λ max: 812

Figure 10:
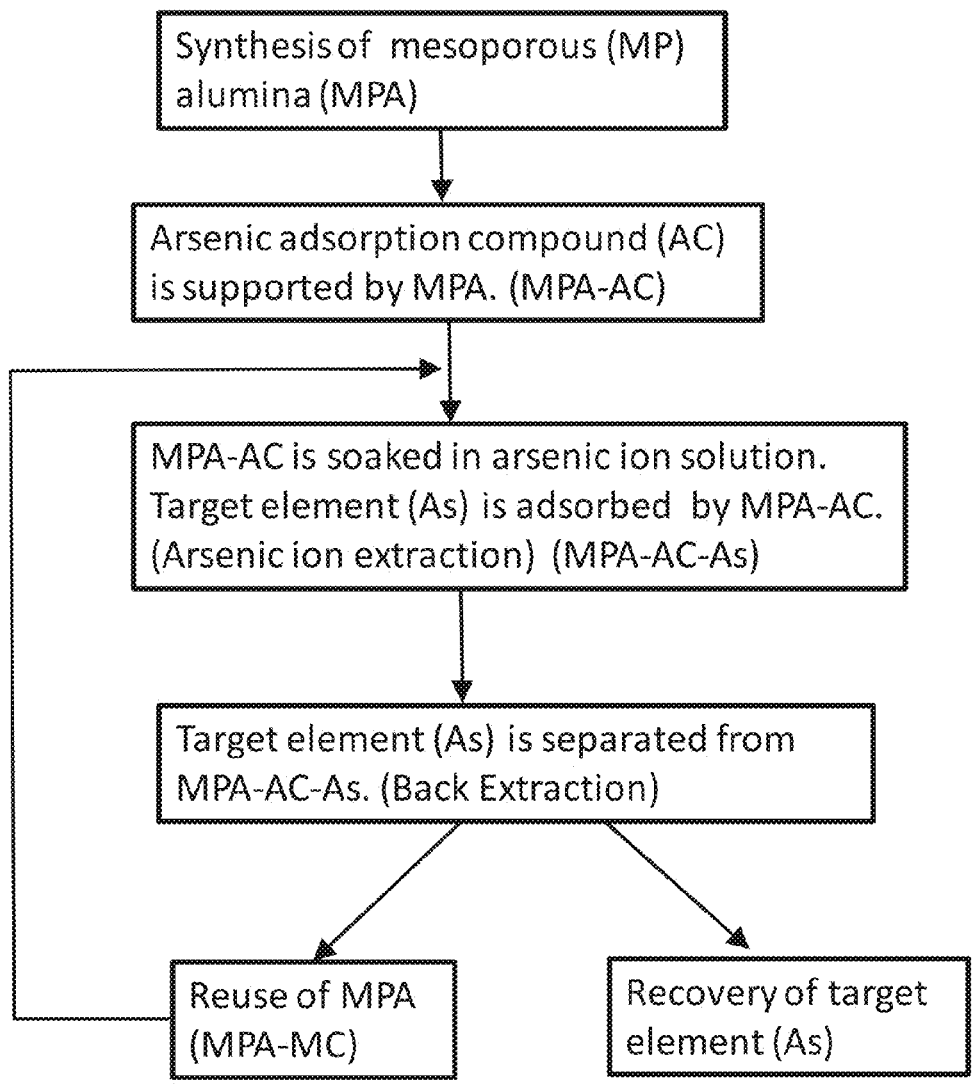
FIG. 10 shows an arsenic recovery system of the invention.

We explain in detail EAA using an alumina nanorod (or it may be called a mesoporous alumina) as the nanostructure material in FIG. 10 to FIG. 30. FIG. 10 shows an arsenic recovery system of this invention. Firstly, a mesoporous alumina, which may be called "MPA" below, is synthesized at first stage. Here, the mesoporous alumina is a kind of porous alumina, and has a mesopore area, which has many small pores (or mesopores) that is 2 to 50 nm in size and has almost uniform and regular diameter. Also, the mesoporous alumina is a porous substance group that is known to have various characteristic by a network patter that the pores form (that is, apace symmetry) and the prepared methods etc. However, we also call a porous alumina having a smaller micropore (pore below 2 nm) than a mesopore or a larger macropore (pore over 50 nm) than a mesopore, a mesoporous alumina.

The mesoporous alumina can be synthesized by various methods. For example, the mesoporous alumina can be prepared with an aluminum acid (for example, aluminum nitrate $\{Al(NO_3)_3\}$, aluminum sulfate $\{Al_2(SO_4)_3\}$, aluminum acetate $\{Al(CH_3COO)_3\}$) and a surfactant {for example, cetyltrimethylammonium bromide (CTAB), camphorsulfonic acid (CSA)}. Or, the mesoporous alumina can be prepared by hydrolyzing an aluminum alkoxide (for example, aluminum isopropoxide) and calicining. The mesoporous alumina is a porous nanotube structural body that has a elongated circular cylindrical shape that is 2 to 50 nm in diameter. But the structure of the mesoporous alumina may be other shapes, for example, rod shape, corn shape, sphere shape, etc. Since the mesoporous alumina is robust in the outer shell and uniform in the shape, it can keep the stable quality even if it is used repeatedly to adsorb arsenic ion by supporting an arsenic ion adsorption compound.

Next, in the second stage, an arsenic ion adsorption compound is supported by the mesoporous alumina, which may be called "MPA". In the second stage, arsenic ion (or other cations or anions) is adsorbed by the arsenic ion adsorption compound. EAA is the mesoporous alumina supporting the arsenic ion adsorption compound. There is a metal complex, an inorganic metal compound, or an organic metal compound as the arsenic ion adsorption compound. Also, the arsenic ion adsorption compound such as a cellulose or a protein is contained. There is an inorganic metal complex, an organic metal complex, a metal carbonyl compound, a metal cluster, or an organic metal compound as the metal complex. Also, a chelate compound is contained. The arsenic ion adsorption compound is a compound that can adsorb arsenic (ion), can be supported by MPA, and can separate arsenic (ion) of the target element by some chemical treatments after separating cations and anions except arsenic ion of the target element by other chemical treatments.

It is desirable that the arsenic ion adsorption compound is a compound that can selectively and heavily adsorb arsenic ion of the target element that we would like to recover. For example, there is the chelate compound that can selectively adsorb arsenic ion. The arsenic ion adsorption compound can selectively adsorb arsenic ion of the target element by adjusting pH value, temperature and concentration in the ion solution that is dissolving various kinds of anions and cations containing arsenic ion. Since the chelate compound can selectively adsorb ultra trace (for example, ppm level to ppb level) of arsenic, it can efficiently and selectively adsorb arsenic ion even if the amount of arsenic ion contained in the ion solution is small.

Or, for example, there is a heteropoly acid as the arsenic ion adsorption compound. There is an ammonium molybdate such as ammonium molybdate tetrahydrate $\{(NH_4)_6Mo_7O_{24}\}$ as the heteropoly acid. The heteropoly acid is supported to the surface of porous nanotube having a large surface area, and it adsorbs molybdenum as poly element and arsenic ion $\{As(V)\}$ as hetero element. Accordingly, since the heteropoly acid has the high preference and the high selectivity to arsenic ion $\{As(V)\}$, the heteropoly acid fits to the extraction (or, recovery) of arsenic ion $\{As(V)\}$ in the solution. (We use "adsorb" or "adsorption" as the word showing the same meaning as "bind" (verb) or "bind" (noun) in this application.)

This invention is regarding the mesoporous alumina (or, EAA) supporting the arsenic ion adsorption compound that is useful to remove and detect arsenic ion {especially As(V) or $As^{5+}$ }. It is known that As(III) ion or $As^{3+}$ exits, and the method to convert As(III) ion $\{As^{3+}\}$ to $As^{5+}$ is a public knowledge in the patent document 8, etc. This invention contains preparing a detective solution and target water containing As(V) ion $\{As^{5+}\}$ converted from As(III) ion $\{As^{3+}\}$ using such the publicly known measures.

Well, in the examples of this invention, the detective solution or the target water made by converting As(III) ion $\{As^{3+}\}$ to As(V) ion $\{As^{5+}$ } using the following methods is used.

1. The methods to convert As(III) ion $\{As^{3+}\}$ to As(V) ion $\{As^{5+}\}$

An oxidation of As(III) ion $\{As^{3+}\}$: The most common method is to use a hydrogen peroxide $(H_2O_2)$, a sodium hypochlorite (NaOCl), a ferric chloride $(FeCl_3)$, and a potassium permanganate $(KMnO_4)$. So, we used only $H_2O_2$ and NaOCl as an oxidation agent.

(1) Oxidation using $H_2O_2$

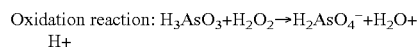

Oxidation reaction: $H_3AsO_3 + H_2O_2 \rightarrow H_2AsO_4^- + H_2O + H^+$ 20 ml solution was made by adding the amount of $As^{3+}$ and 1 ml of 20% $H_2O_2$ to the water.

(2) Oxidation using NaOCl

The oxidation works at pH<7.5.

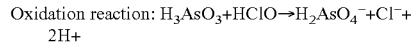

Oxidation reaction: $H_3AsO_3 + HClO \rightarrow H_2AsO_4^- + Cl^- + 2H^+$ 20 ml solution was made by adding the amount of $As^{3+}$ and 1 ml of 10% NaOCl to the water.

There are various method as the method (called "complex method") to support (or modify) such the arsenic ion adsorption compounds to MPA. For example, if the arsenic ion adsorption compounds supported by MPA is natural ion, a reagent impregnation method is used. If the arsenic ion adsorption compound supported by MPA is anionic, a cation exchange method is used. If the arsenic ion adsorption compound supported by MPA is cationic, an anion exchange method is used. These complex methods are not especial conditions or operations, but belong to the well-known and general technical field. Accordingly, regarding the detail explanation of these general technical fields, the review papers, documents in the solid adsorption field, etc. can be referred to.

As the method to support ammonium molybdate as the heteropoly acid to MPA nanotube of the porous nanosubstructure, there is the method to prepare an alumina (arsenic)-captor that supports ammonium molybdate on the surface of the nanostructure in the nanotube, etc. of the mesoporous alumina by contacting with ammonium molybdate solution after functionalizing the nanotube surface of the mesoporous alumina using a surfactant such as DDAB (dilauryl dimethyl ammonium bromide). Here, the term "captor" may be used below in the meaning that it captures (adsorbs) arsenic ion.

Though the arsenic ion adsorption compounds may selectively adsorb arsenic ion of the target element by itself, that is, without supported by MPA, in such case, they cannot use efficiently the functional groups because they aggregate. Even if arsenic ions of the target element adsorb to the functional group existing on the surface of the arsenic ion adsorption compounds that are aggregated (for example, a massive form substance), it is much difficult to adsorb arsenic ions to all functional group in the arsenic ion adsorption compounds existing inside the massive form substance, since the arsenic concentration inside the massive form substance of the arsenic ion adsorption compounds decreases exponentially with the square of the distance of the surface because arsenic ions diffuse or sink into the inside of the massive form substance. Furthermore, even though arsenic ions are adsorbed to the functional group of the arsenic ion adsorption compounds, it is much difficult to remove (separate or elute) the arsenic ions adsorbed. Though arsenic ions can diffuse into the inside of the massive form substance and be removed from the inside by a long time treatment, this process cannot be adopted industrially since it is non-productive that arsenic ions move in the inside of the massive form substance.

In contrast, since the mesoporous alumina (MPA) has a very large pore surface area and highly-ordered orientation structure, MPA can support the arsenic ion adsorption compound on the surface and the internal wall of MPA. As a result, since the arsenic ion adsorption compounds supported are orderly arranged and bound, the adsorption capability of arsenic ion becomes much high. That is, one molecular of the arsenic ion adsorption compounds can be utilized as an arsenic ion adsorption site. Since arsenic ion solution or back extraction solution easily and rapidly seeps into the surface and the pore inside of MPA, it easily and rapidly contacts with the arsenic ion adsorption compounds supported by MPA. This means that arsenic ion can be adsorbed rapidly as soon as the arsenic ion adsorption compounds supported by MPA contact with the arsenic ion solution. This also means that arsenic ion adsorbed by MPA can be rapidly separated from MPA by contacting with the back extraction solution (the elution solution) when arsenic ion adsorbed is separated. As a result, the productivity improves dramatically.

Next, in the third stage, the mesoporous alumina (MPA) supporting densely the arsenic ion adsorption compounds (which may be termed "AC"), which may be termed "MPA-AC"), is contacted with (or soaked in) the arsenic ion solution containing arsenic ion. The arsenic ion solution contains arsenic ion, but it may contain other cations and anions. In this invention, it is the solution obtained by dissolving arsenic ion contained in the stone using acid or alkali, etc. to separate arsenic from the stone, or it is a natural water dissolving arsenic existing in the environment, etc., or it is an industrial effluent, etc. containing arsenic ion. Especially, the concentration of arsenic ion must be reduced less than the tolerance limit to use as the agricultural water, the drinking water, and the daily life water. Accordingly, the system using MPA-AC of this invention can be preferably applied because the MPA-AC can adsorb arsenic ion of wide concentration range of ppm-ppb-ppt level.

Though the arsenic ion solution contains arsenic ion of the target element, other cations, and anions, since MPA-AC of the present invention adsorbs selectively and preferentially arsenic ion of the target element under specific conditions (pH value, temperature, concentration, etc.), MPA-AC adsorbing arsenic ion of the target element (that is, MPA-AC-As) can be obtained by soaking MPA-AC in the arsenic ion solution under the specific conditions. However, since other ions (it may be termed "M") except arsenic ion may be possibly adsorbed by small variation of the conditions, MPA-AC-As of which the adsorption amount of the ions except arsenic ion is very small can be obtained by reducing beforehand the amount of ions except arsenic ion of the target element in the arsenic ion solution. For example, there is a method to remove the ions except arsenic ion by precipitating them using the pH adjustment or the chemical treatment in the arsenic ion solution.

The mesoporous alumina supporting ammonium molybdate on the nanotube surface of the mesoporous alumina, which may be called alumina captor or MPA-AC, can adsorb significant amount of arsenic ion by soaking and stirring in the arsenic ion solution for a fixed time (for example, 5-10 hours) at room temperature (0° C.-40° C.). The alumina captor (MPA-AC) can adsorb arsenic ion only by soaking and stirring in the arsenic ion solution (containing tap water or natural water) containing arsenic ion, even though the especial pretreatments (pH control before adsorption, the treatment to remove other ions, or the treatment to add a special agent, etc.) and/or heating and/or pressuring are not done. Accordingly, since arsenic ion can be removed from arsenic ion solution using simple equipments and/or facilities, the productivity of the arsenic ion removal increases and the cost of the arsenic ion removal can be reduced. Also, since the energy consumption of the arsenic ion removal doe not increase, this invention is good for the environment. Because arsenic (ion) is removed from a filtrate, the filtrate can be used as a drinking water or it can return to the environment and the natural world.

If the initial arsenic ion concentration in the arsenic ion solution Y, and X % of the arsenic ion is removed by one contact treatment of MPA-AC in the solution, that is, the removal efficiency of arsenic ion is X %, the arsenic ion concentration in the arsenic ion solution in two contact treatments is $Y(1-X/100)^2$. For example, if X=90, the arsenic ion concentration is 0.01Y for two contact treatments, it is 0.0001Y for four contact treatments. Arsenic ion concentration in the solution can be made less than the tolerance limit by multi steps of contact treatments. Since it can be simply actualized without the special equipments and facilities, the low cost can be realized. Furthermore, since special agents, etc. are not used, the removal and harmless treatment of the special agents, etc. are not needed in the solution (that has the arsenic ion concentration less than tolerance limit) after the removal treatment of arsenic ion. As a result, for example, the solution can be used as a drinking water. These show that our removal system can realize the low cost.

Next, in the forth stage, arsenic ion of the target element is separated from MPA-AC-As by contacting (or soaking) MPA-AC-As, which is adsorbing only arsenic ion of the target element, with the solution (the eluted solution) that can dissolve (elute) arsenic ion of the target element. (elution treatment) Or, only arsenic ion of the target element may be eluted by the adjustment of the conditions such as pH value, temperature and solution concentration, etc. Or, only arsenic ion of the target element can be eluted by soaking MPA-AC-As in the solution that can dissolve only arsenic ion. In such cases, it is not necessary to make MPA-AC-As adsorbing only arsenic ion of the target element. If ions except arsenic ion is adsorbed (that is, in the case of MP-AC-As-M), the treatment to remove the ion M is needed before or after arsenic ion is removed from MPA-AC. After that, because MPA-AC separating arsenic ion of the target element is solid, it can be removed from the eluted solution by filtration. MPA-AC removed as solid can be reused. Since only arsenic ion is dissolved in the filtrate, arsenic of the target element can be recovered by separating arsenic of the target element from the filtrate using various methods (for example, electrolytic plating process). Since to prepare MP-AC-As by adsorbing arsenic ion of the target element to MPA-AC can be considered to be an extraction of arsenic of the target element, it can be said that the process is the back extraction process because MPA-AC-As changes to MP-AC by eluting As from MPA-AC-As. For example, to elute As ion from As ion adsorbed by MPA supporting the above ammonium molybdate (that is, MPA-AC-As), the MPA-AC-As may be soaked and stirred in the alkali solution (for example, NaOH solution). Next, by filtrating and washing and drying, MPA-AC can be recovered. The recovered MPA-AC can be reused repeatedly because of the As ion adsorption. As mentioned above, the arsenic ion adsorption compound is a complex molecule which can extract As from an aqueous solution including As and other metals and MPA-AC can separating As from MPA-AC-As.

Example 6

Preparation of Mesoporous Alumina $Al_2O_3$-I

Figure 11:
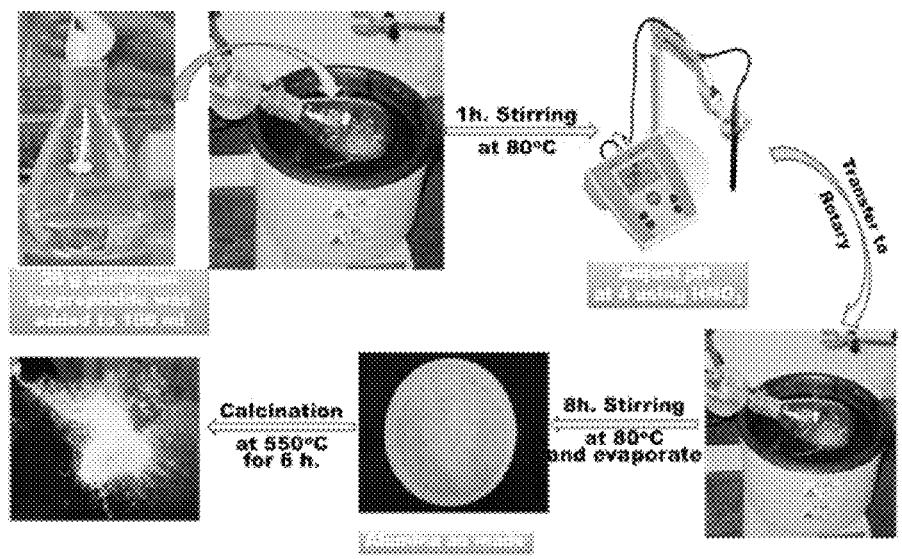
FIG. 11 shows one embodiment of a method to prepare the alumina ($Al_2O_3$) used in the invention.

FIG. 11 shows one of many embodiments regarding preparation methods of Alumina ($Al_2O_3$) used in this invention. As shown in FIG. 11, 20 g aluminum isopropoxide ($C_9H_{21}AlO_3$) was added to 100 ml distilled water in a round flask under magnetic stirring at 80° C. for one hour. Then the pH value of the solution was adjusted to 4 with nitric acid. This mixture was transferred again and stirred for 8 h. at 80° C. After filtering the solution through evacuation, the white material was collected and was allowed to complete the drying process at 60° C. overnight. The organic moieties were removed by calcination at 550° C. in air for 6 h. The white powder get by the calcination is Alumina ($Al_2O_3$). This Alumina is named as $Al_2O_3$-I in the present application. Of course, since the above is an example, numerical value may be changed in some degree. The same can be said for the following examples.

Example 7

Figure 12:
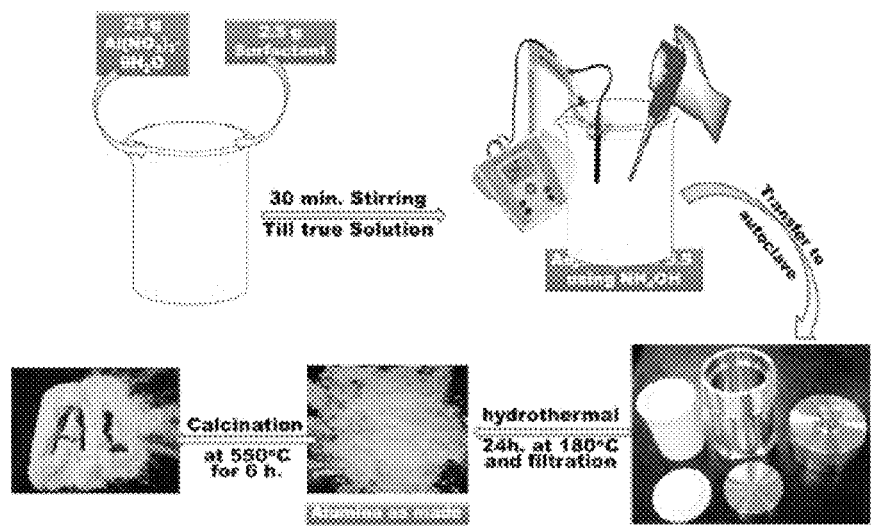
FIG. 12 shows a synthesis process to prepare $Al_2O_3$-II and $Al_2O_3$-III using a surfactant.

Preparation of Mesoporous Alumina $Al_2O_3$-II 25 g Aluminum nitrate ($Al(NO_3)_3.9H_2O$) and 2.5 g Camphorsulfonic acid (CSA) that is a surfactant agent were mixed and dissolved in 75 ml distilled water under magnetic stirring. Then the pH value was adjusted to 5.5 with ammonia solution. After stirring 10 min, the mixture became viscous, and then it was transferred to a Teflon™-lined autoclave for hydrothermal at 160° C.-180° C. for 24 hrs. After cooled to room temperature, the solid material was collected using centrifugation, washed with ethanol several times. The white powder product was obtained and dried at 60° C. overnight, then the organic moieties were removed by calcination at 550° C. in air for 6 hrs. The white powder get by the calcination is Alumina ($Al_2O_3$). This Alumina is named as $Al_2O_3$-II in the present application. FIG. 12 shows a embodiment that represents a synthesis process of $Al_2O_3$-II at pH5.5 with the above surfactant agent. The $Al_2O_3$ is a mesoporous $Al_2O_3$ made with the surfactant agent.

Example 8

Preparation of Mesoporous Alumina $Al_2O_3$-III

Mesoporous alumina was prepared using cetyltrimethylammonium bromide (CTAB), which is a surfactant, instead of surfactant CSA. Namely, as shown in FIG. 12, 25 g Aluminum nitrate ($Al(NO_3)_3.9H_2O$) and 2.5 g CATB that is a surfactant agent were mixed and dissolved in 75 ml distilled water under magnetic stirring. Then the pH value was adjusted to 5.5 with ammonia solution. After stirring 10 min, the mixture became viscous, then it was transferred to a Teflon™-lined autoclave for hydrothermal at 160° C.-180° C. for 24 hrs. After cooled to room temperature, the solid material was collected using centrifugation, washed with ethanol several times. The white powder product was obtained and dried at 60° C. overnight, then the organic moieties were removed by calcination at 550° C. in air for 6 h. The white powder get by the calcination is Alumina ($Al_2O_3$). This Alumina is named as $Al_2O_3$-III in the present application. The $Al_2O_3$-III is a mesoporous $Al_2O_3$ made with the surfactant agent.

Example 9

Characterization of Mesoporous Alumina (X-Ray Diffraction)

Figure 13:
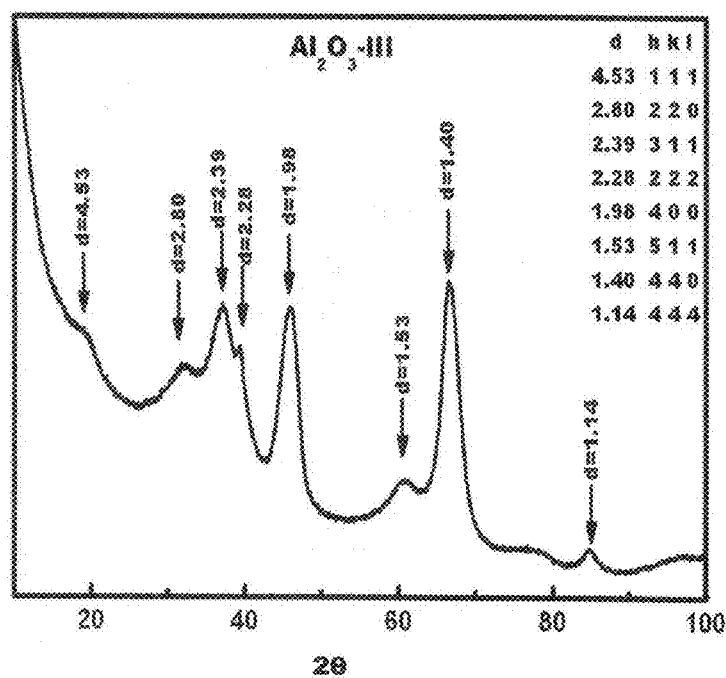
FIG. 13 shows a wide-angle X-ray diffraction (XRD) pattern of the mesoporous Alumina.
Figure 14:
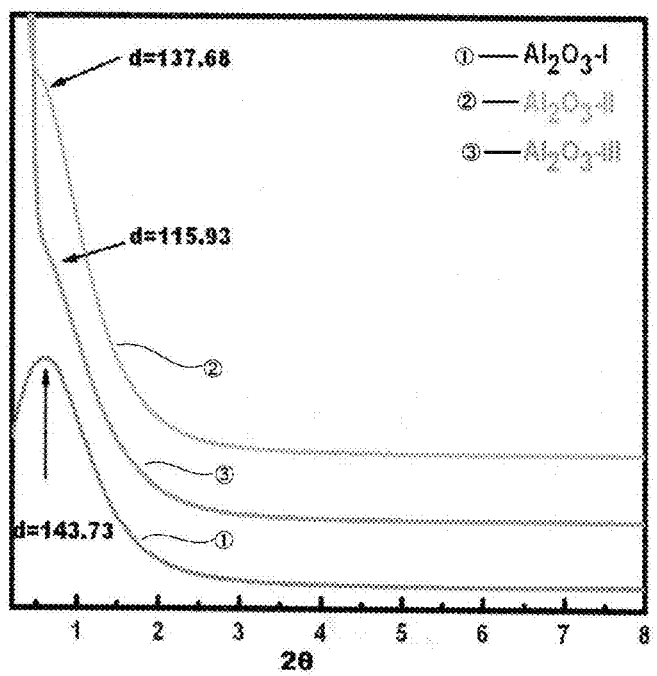
FIG. 14 shows a small angle X-ray scattering (SAXS) pattern of the mesoporous Alumina.

FIG. 13 shows wide-angle X-ray diffraction (XRD) pattern of the mesoporous Alumina. FIG. 14 shows Small angle X-ray scattering (SAXS) pattern of the mesoporous Alumina.

The crystal structure of the calcined alumina made in the examples 6 to 8 powder was characterized using XRD and SAXS. FIG. 14 shows the measurement results of Small angle X-ray scattering patterns of three kinds of Alumina ($Al_2O_3$-I, $Al_2O_3$-II, $Al_2O_3$-III). The small-angle X-ray profiles of the mesoporous alumina nanotubes showed broadly resolved diffraction peaks in the region $0.45° \leq 2\theta \leq 1.45°$, (110) lattice spacing (d) is respectively approximately 14.373 nm, 13.768 nm, and 11.593 nm for $Al_2O_3$ without a surfactant, with CTAB and CSA surfactants. The broadening and low-resolution peaks with less intensity indicated the formation of disordered alumina mesostructure. Accordingly, the level of the mesoporous of $Al_2O_3$-I is low, those of $Al_2O_3$-II and $Al_2O_3$-III are high. These show the effect of usage of the surfactant agent during formation of alumina.

FIG. 13 shows a wide-angle X-ray diffraction (XRD) pattern of mesoporous Alumina ($Al_2O_3$-III) prepared with a surfactant CTAB. The X-ray diffraction patterns (hkl) of alumina could be assigned to all diffraction peaks using an inset method of crystal lattice spacing. That is, peak positions were specifically determined by using single crystal diffractometer output conversion software (DIFRAC plus Evaluation Package (EVA) software) with a powder diffraction database (PDF-2 Release 2009 databases). As known from FIG. 13, the wide angle XRD pattern shows well-resolved and distinctive diffraction peaks of $Al_2O_3$-III. It indicates the formation of single-phase $\gamma$-$Al_2O_3$ with crystalline structures, and is consistent with $Al_2O_3$ (JCPDS No. 029-0063) indicated in JCPDS card charts. Also, a lattice constant is a=7.924 Å. In conclusion, the boarding and low resolution of the low intensity peaks indicated the formation of the short-range order $\gamma$-$Al_2O_3$ mesostructures.

Example 10

Characteristics of Methoporous Alumina (Nitrogen Adsorption Isotherms)

Figure 15:
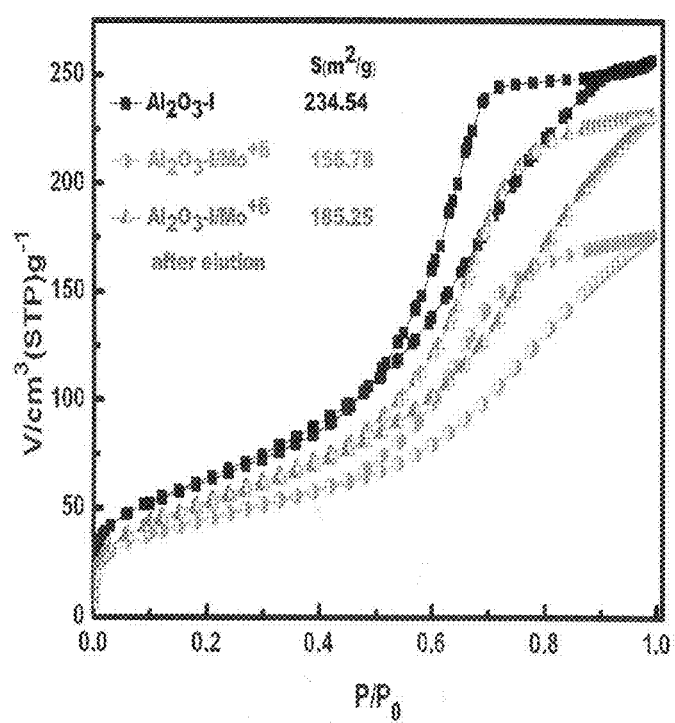
FIG. 15 shows the Nitrogen ($N_2$) adsorption/desorption isotherms of the mesoporous alumina at Temperature 77K.

We could control the shape and size of alumina materials by using the method shown in the example 6-8. Further their evidences can be obtained from the $N_2$ adsorption isotherm. FIG. 15 shows Nitrogen ($N_2$) adsorption/desorption isotherms at Temperature 77K. The horizontal axis is a relative pressure and the vertical axis is an adsorbed amount. The $N_2$ adsorption isotherms show that typical type IV adsorption behavior in the classification according to IUPAC and a pronounced hysteresis loop with a well-known sharp inflection of adsorption/desorption branches were features of the isotherms of alumina samples and are characteristics of the uniformity and regularity of alumina materials as shown in FIG. 15. The alumina samples exhibited $H_2$ hysteresis loops which are typical for uniform mesoporous cubic structure that fabricated in the presence and absence of surfactant. The well-characterized sharp inflection point appeared at 0.5≤P/P0≤0.85.

Figure 16:
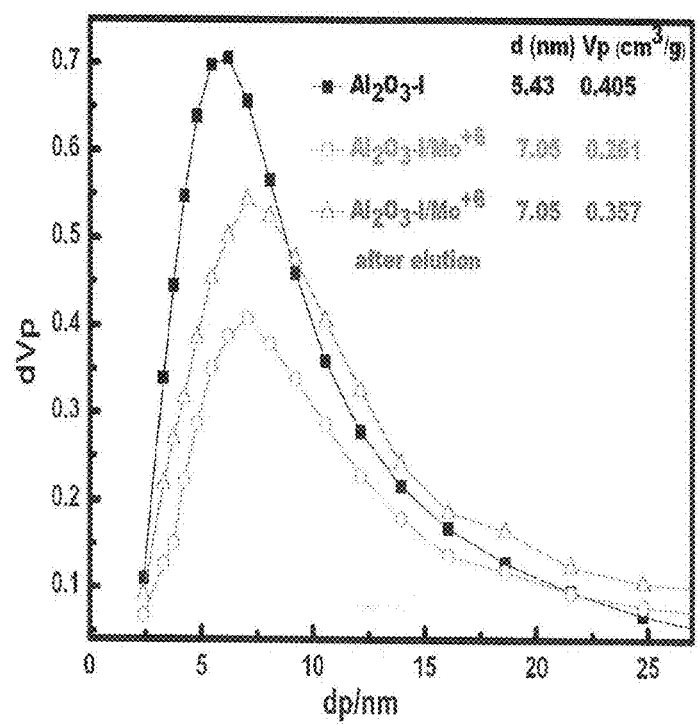
FIG. 16 shows the micropore distributions of the mesoporous alumina.

FIG. 16 shows micropore distributions at Temperature 77K obtained from the Nitrogen (N2) adsorption/desorption isotherms of FIG. 15. The horizontal axis is pore diameter and the vertical axis is differential value dVp. The sharpness in the Nitrogen ($N_2$) adsorption/desorption isotherms of FIG. 15 shows the rapid increase of the adsorption amount and indicates capillary condensation within uniform mesoporous in the approximate 5.43 nm that is a pore size peak of $Al_2O_3$-I. Moreover, the Molybdenum ion ($Mo^{+6}$)-modified alumina material shows that decreasing in the width of the hysteresis loop indicated the decrease in the nanoscale pore size with all of the fabricated nanoprobes, as shown in the $N_2$ adsorption isotherms data. In this synthetic design, the alumina mesostructure exhibited appreciable textural parameters, namely, specific surface area and pore volume were obtained. Our results indicate that the total pore volumes are 0.405 $cm^3\ g^{-1}$, 0.261 $cm^3\ g^{-1}$ and 0.357 $cm^3\ g^{-1}$ for $Al_2O_3$-I, $Al_2O_3$-I modified with $Mo^{+6}$ and $Al_2O_3$-I modified with $Mo^{+6}$ after elution of As, respectively. Also, the BET specific surface area are 234.54 $m^2\ g^{-1}$, 156.78 $m^2\ g^{-1}$ and 185.25 $m^2\ g^{-1}$ for $Al_2O_3$-I, $Al_2O_3$-I modified with $Mo^{+6}$ and $Al_2O_3$-I modified with $Mo^{+6}$ after elution of As, respectively. The BET specific surface area of $Al_2O_3$-I that does not support ammonium molybdate is large (234.54 $m^2\ g^{-1}$). Since the change of the inflection of $Al_2O_3$-I modified with ammonium molybdate is small, it turns out that the mesostructure of alumina does not much change before and after $Al_2O_3$-I is modified with ammonium molybdate. Furthermore, it turns out that the mesostructure of alumina does not much change after arsenic ions are adsorbed to ammonium molybdate supported by $Al_2O_3$-I alumina and after the arsenic ions adsorbed are eluted. Accordingly, it is shown that the mesostructure of alumina is stable before and after the process.

Example 11

Characterization of Mesoporous Alumina (Transmission Electron Microscopy (TEM))

Figure 17:
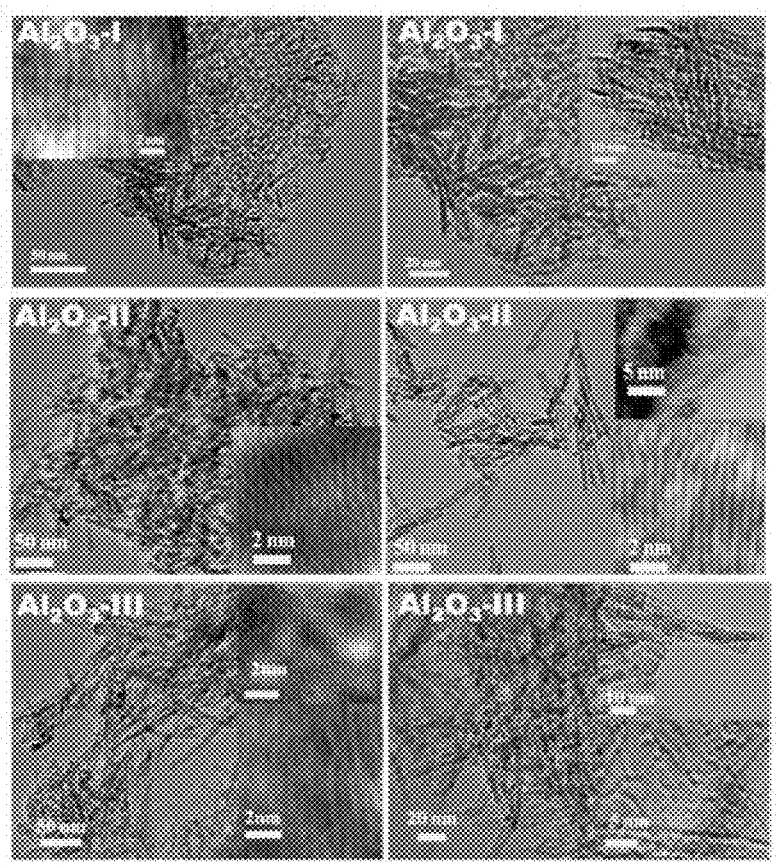
FIG. 17 shows the representative TEM images of the mesoporous alumina structures.

FIG. 17 shows representative TEM images of uniformly-shaped mesoporous alumina structures. The high resolution transmission electron microscope (HRTEM) of the mesoporous alumina was performed to investigate the controlled morphology, the mesoporosity and crystal structure of alumina oxide. The above photographs are for $Al_2O_3$-I, the middle photographs are for $Al_2O_3$-II, and the below photographs are for $Al_2O_3$-III. As can be seen from these HRTEM micrographs of FIG. 17, they reveal the formation of porous alumina nanotubes spindled with diameter range 5-8 nm. The crystal structure representative oriented with the preferable [222] incidence provided direct evidence of the formation of large-scale nanocrystal domains with cubic Fd3m symmetry. The most prominent feature was that the mesostructure of alumina showed uniform arrangements and continuous ordering of lattice fringes over large-scale regions without distortion. Large-scale nanocrystal domains along the incidences are characteristic of alumina cubic lattice nanotubes. The TEM micrographs, in general, the HR-TEM images clearly reveal large domain sizes of ordered face centered cubic mesoporous networks.

Example 12

Facile Fabrication Alumina ($Al_2O_3$) Captors

Figure 18:
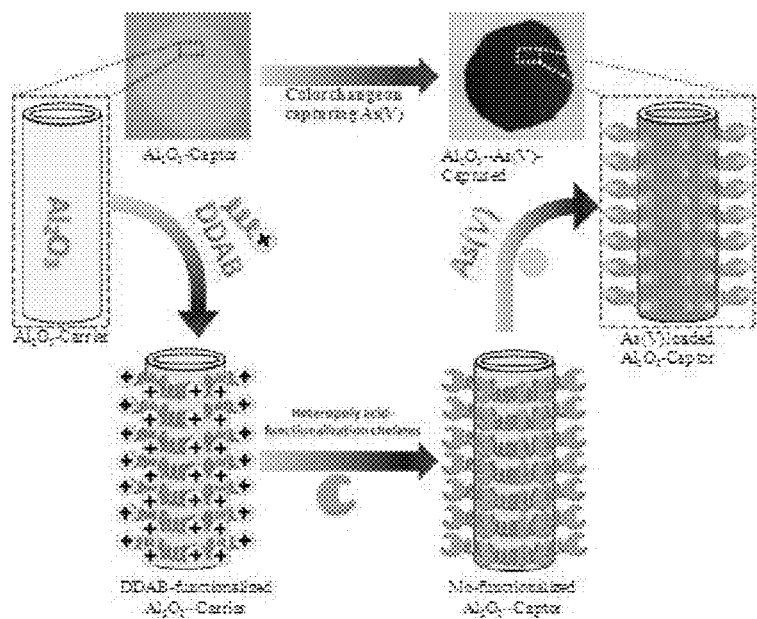
FIG. 18 is a figure drawn schematically that indicates the process flow from the fabrication of the alumina-captor to the arsenic ion adsorption of the alumina captor.

The present invention is based on utilizing the remarkable characteristics of aluminum metal oxides (alumina: $Al_2O_3$) that can support Arsenic ion adsorption compound, namely which can be used as a carrier of arsenic (V) (or As(V) captor). The Arsenic ion adsorption compound is a compound that adsorbs arsenic ion, and it is called alumina-captor of arsenic (ion) or merely (Alumina-) captor. Captor means a material or a substance that captures something like arsenic ion. Producing the alumina at large scale was investigated and as shown in FIG. 18, it is found to be easy to produce the alumina as there are no complicated machines. FIG. 18 is a figure drawn schematically that indicates a series of process flows to adsorb arsenic ion using $Al_2O_3$-captor, which is the highly functionalized mesoporous $Al_2O_3$ supporting arsenic ion adsorption compound, namely it is a schematic figure that indicates a flow from a fabrication of alumina-captors till an adsorption of arsenic ion to the alumina-captor. For instance, the polarity of the $Al_2O_3$ surface matrices, which was fabricated in the examples 6-8, was first fine-tuned by the dense dispersion of cationic surfactant such as dilauryl dimethyl ammonium bromide (DDAB) as shown in FIG. 18. The processing functionalizes circumferences of the mesoporous alumina nanotubes. This state is an alumina carrier ($Al_2O_3$-Carrier) shown in FIG. 18. Here carrier is also used in the meaning of captor.

The appropriate treatment for the alumina by heteropoly acids such as ammonium molybdate, for example, Ammonium molybdate tetrahydrate, led to the functionalization of pore surface of mesoporous alumina and the heteropoly acids was supported to the surface. Then, the solvents and other reagents were removed by simple evacuation using the rotary evaporator. After 10-20 min, all the process was finished and powdered alumina supporting heteropoly acids (or modified with heteropoly acids) was fabricated. The powdered alumina is the captor of arsenic, and it can adsorb arsenic (As(V)) by contacting with the solution containing arsenic (As(V)). Since the mesoporous alumina that adsorbed arsenic (As(V)), which is $Al_2O_3$—As(V)-captured in FIG. 18, gets discolored, the absorption of arsenic (As(V)) can be seen by the naked eye.

A procedure in which the alumina ($Al_2O_3$-I, $Al_2O_3$-II, $Al_2O_3$-III) supports the above ammonium molybdate is explained in detail as follow. 1 mg alumina and 0.3 mg surfactant DDAB in 40 ml ethanol were mixed and stirred, then they were sucked and exhausted for 30 minutes at 35° C. by a rotary evaporator. Next, they were vacuumed and dried at 45° C. by the vacuum pump of the rotary evaporator. The solid obtained was washed, and dried at normal pressures and at 45° C. The solid obtained was mixed in the solution in which 0.3 mg ammonium molybdate $\{(NH_4)_6Mo_7O_{24}24H_2O\}$ was mixed in 50 ml water, and was stirred for 12 hours. The mixed solution was filtrated. The solid obtained was washed and was vacuumed and dried at 55° C. Alumina-(As)-captor supporting ammonium molybdate $\{(NH_4)_6Mo_7O_{24}\}$ on the surface of the mesoporous alumina can be prepared by the above procedure.

Example 13

Applicability of Alumina ($Al_2O_3$)-Captor to Arsenic Ion Aqueous Solution

The new technique is based on utilizing the unique high potential of As(V) to form stable complex with molybdenum compounds that are supported by the mesoporous alumina nanotubes. Furthermore, the Alumina ($Al_2O_3$) supporting the complex takes on a blue color by the addition of small amount of dilute solution of ascorbic acid (for example, 0.1 mole (M)) to the solution containing the complex. The blue color strength increases with the arsenic amount adsorbed and can be also detected by naked-eye. It is well know that this kind of complex can be formed only in acidic conditions. Asrcenate-molybdenate-complex can be also formed in aqueous solution in the state supported by alumina ($Al_2O_3$), as shown in FIG. 19.

Figure 19:
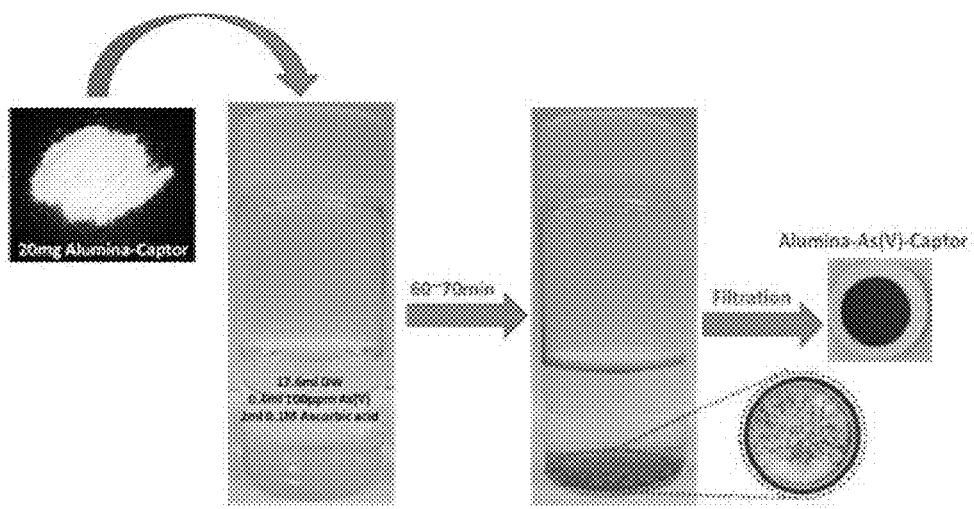
FIG. 19 shows a method to recover arsenic from the solution dissolving arsenic ion using the alumina-captor.

FIG. 19 shows a method to recover arsenic from the solution dissolving arsenic (As(V)) using Alumina-captor. The procedure is as follows.

(1) 17.6 ml aqueous solution, 0.4 ml of 100 ppm As(V) solution, and 20 mg of the alumina-captor were added to 50 ml caped flat bottomed bottle equipped with magnet stirrer. The alumina-captor is the alumina ($Al_2O_3$-I, $Al_2O_3$-II, $Al_2O_3$-III) supporting the above Ammonium molybdate tetrahydrate.

(2) The mixture containing the alumina-captor was stirred well using magnetic stirrer for 30 min at 45° C.

(3) After the incubation period (30 min) was finished, 2 ml of 0.1M ascorbic acid was added to the solution and leaded to 2 ppm final concentration of As(V).

(4) Stirring was continued for more 30-40 min, the alumina-collector (alumina-captor) took on a blue color by adsorbing arsenic ion and the formation of arsenate-molybdenate-complex. Accordingly, the blue color observed indicates the detection of the As(V) by the alumina-collector (alumina-captor).

(5) The solid was filtered using filter paper GF/C 25 mm ø circles supplied by Whatman™, and washed with deionized water.

(6) The solid obtained was a clear blue colored alumina-captor that adsorbed As(V). This indicates the success of collecting the As(V) from the solution.

Figures 20, 21:
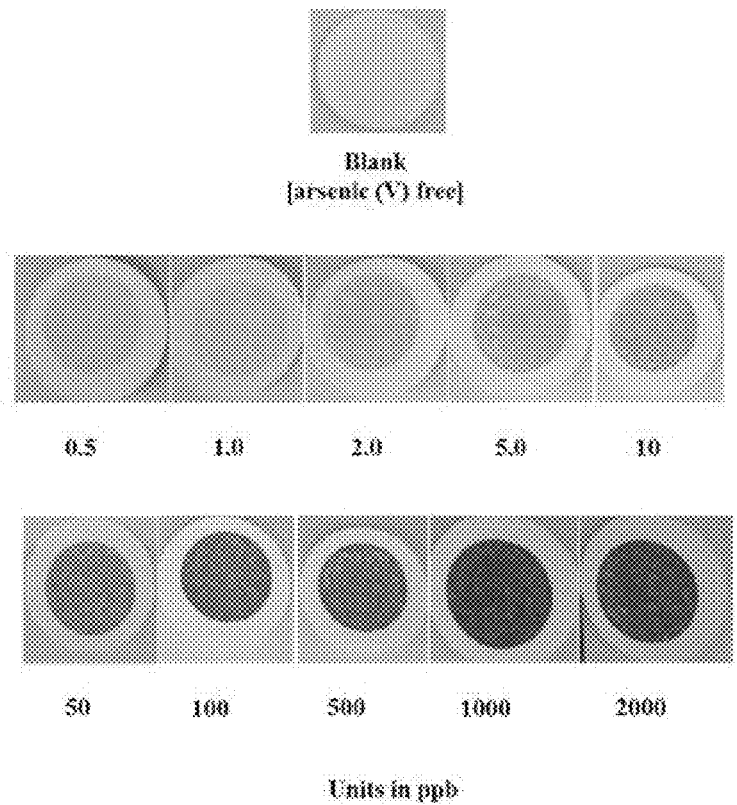
FIG. 20 is a table that shows the arsenic ion concentration in the solution.
FIG. 21 shows the color reaction of the alumina-captor after filtering the solutions having the various arsenic concentrations.

(7) The arsenic ion concentration in the solution was measured using Inductively-coupled plasma optical emission spectrometry (ICP-OES) at each stage. FIG. 20 is the table that shows the arsenic ion concentration in the solution at each stage. The arsenic ion concentration in the original solution was 2.035 ppm, and that in the solution after the alumina-captor was dipped into the solution was 0.636 ppm, therefore 1.363 ppm arsenic ion in the solution was removed by the alumina-captor. Accordingly, the removal efficiency of arsenic ion by the alumina-captor is approximately 67%.

Example 14

Ultra-Sensitivity Capture to ppt Level of Concentration

The detection limit of arsenic concentration by the traditional detection methods and removal methods of arsenic is up to $10^{-6}$M, namely ppm level. However, the alumina-captor of the present invention is not only easy to prepare but also can detect or remove ppb-ppt level of arsenic. FIG. 21 shows the color reaction of alumina-captor after filtering the solutions having various arsenic concentrations. The alumina-captor that adsorbed arsenic was obtained by adding the alumina-captor to the solution containing the various concentrations of arsenic ion prepared according to the method shown in FIG. 13. Though the color of the alumina-captor is white in the case where the alumina-captor does not contain arsenic, it changes blue in the case where the alumina-captor contains arsenic. Furthermore, as arsenic (ion) concentration increases, the blue color becomes deeper. That is to say, since the color of the alumina-captor changes a little light blue in the case where the alumina-captor adsorbed 0.5 ppb ($10^{-10}$M) arsenic, it can be recognized by the naked eye that the alumina-captor adsorbed arsenic. The color in 100 ppb arsenic (ion) concentration is blue, and the color in 2000 ppb arsenic (ion) concentration is dark blue. As shown in FIG. 21, as the arsenic concentration increases, the blue color turns deeper continuously. That is, the intensity of the blue color increases the higher concentration of arsenic. Lower limit nearly $10^{-10}$M indicated the ultra-sensitivity of the novel alumina-captor for detecting arsenic (V). In other words, we can know the arsenic concentration of the alumina-captor by the color of the alumina-captor that adsorbed arsenic (ion). As can be seen from FIG. 8 or Table 5, we can know the arsenic ion concentration in the solution from a change of optical properties such as a ultraviolet-visible spectrophotometry (The nanostructures of the present invention support As ion adsorption compound (receptor) changing the optical properties.) by using the nanostructures of the present invention (As adsorption device or EAA) supporting As ion adsorption compound. Accordingly, including the detection of arsenic ion concentration by the color change, As adsorption device of the present invention As adsorption device is very useful as a detective sensor of arsenic ion utilizing optical properties.

From the above mention, the alumina-captor of the present invention can not only remove arsenic ion in the solution, but also use as the detective sensor of arsenic (ion) concentration. In addition, since the detective sensor of arsenic concentration can detect the ppb-ppt level of arsenic concentration, it can detect trace of arsenic in the environment and it can judge whether the concentration is a problem. Also, since the alumina-captor of the present invention can adsorb ppt level of trace of arsenic ion in the environment, a very small amount of arsenic ion (nearly $10^{-10}$M) in the environment can be removed. As a result, Arsenic (As)-free environment can be realized. Beside the novel structure of the alumina-captor and their facile fabrication as nano-captors, their high sensitivity toward trace concentrations (~$10^{-10}$ M) of arsenic (As(V)) is very interesting and appreciated compared to other existing collectors or detectors with detection limit up to ($10^{-6}$M). In the present invention, after the mesoporous alumina is prepared, the arsenic ion adsorption compound is supported by the mesoporous alumina, then arsenic ion is adsorbed to the arsenic ion adsorption compound. Namely, it can be said that the present invention is a building-block technique. The great advantage of the high sensitivity of arsenic ion detection or adsorption by the mesoporous alumina supporting the arsenic ion adsorption compound may attribute to the high mobility and flexibility of the electron acceptor/donor of the immobilized receptor which was fully controlled by the new building-block technique.

Example 15

High Selectivity by Collecting Arsenic as (V) from Multi-Cations Aqueous Solution We investigated the selectivity for adsorbing arsenic ion by the alumina-captor of the present invention, namely we investigated whether the other metal ions affect the selectivity of the As adsorption in the existence of multi competitive metal ions. The procedure is as follows.

(1) To 50 ml caped flat bottomed bottle equipped with magnet stirrer, 16 ml aqueous solution, 0.2 ml of 100 ppm As(V) solution, 100 µm of each 200 ppm stock solution of the following cations, [$Na^+$, $Ca^{+2}$, $Mg^{+2}$, $Li^+$, $Ho^{+3}$, $Co^{+2}$, $Zn^{+2}$, $Ni^{+2}$, $Cd^{+2}$, $La^{+2}$, $Mn^{+2}$, $Hg^{+2}$, $Ba^{+2}$, $Cu^{+2}$, $Al^{+3}$, $Cr^{+6}$, $Fe^{+2}$, and $Bi^{+3}$] [totally 1.8 ml], and 20 mg alumina-captor were added. The individual concentration of each metal cation was kept at 1 ppm. Here, the alumina-captor is the alumina ($Al_2O_3$-I, $Al_2O_3$-II, $Al_2O_3$-III) supporting the above Ammonium molybdate tetrahydrate.

(2) The mixture was stirred well using magnetic stirrer for 30 min at 45° C.

(3) After the incubation period (30 min) was finished, 2 ml of 0.1M ascorbic acid was added to the solution.

(4) Stirring was continued for more 30-40 min, where the blue color of the alumina-captor was observed, That indicates the detection and adsorption of the As(V) by the alumina-captor.

(5) The solid was filtered using filter paper GF/C 25 mm ø circles supplied by Whatman™, and washed with deionized water.

(6) A clear blue alumina-captor was obtained. That indicates the success of collecting the As (V) from the solution containing As (V).

Figure 22:
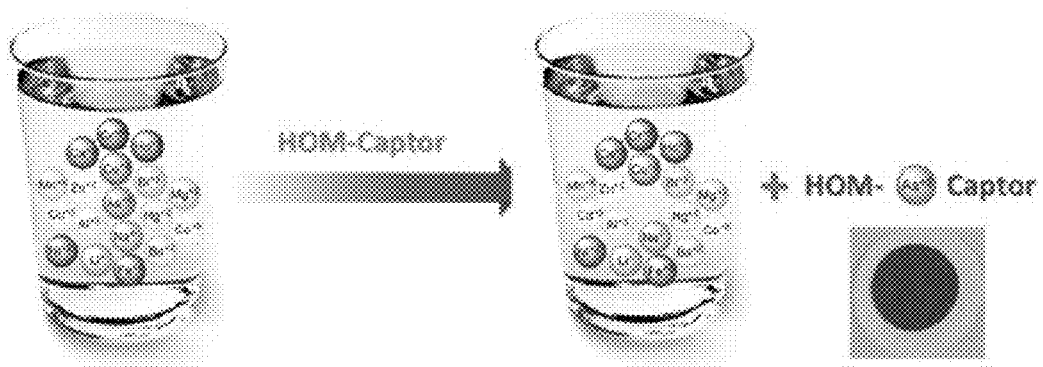
FIG. 22 is a schematic drawing that shows a state where the alumina-captor of the present invention adsorbs arsenic ion from the aqueous solution containing various metal ions.

FIG. 22 is a schematic drawing showing a state where the alumina-captor of the present invention adsorbs only arsenic ion from the aqueous solution containing various metal ions. In FIG. 22, HOM means "High Ordered Mesoporous" and a mesoporous alumina in the present invention. After the HOM-captor (or alumina-captor) of the present invention is added to the solution dissolving many metal ions containing arsenic ion, only arsenic ion is selectively and preferentially adsorbed by the HOM-captor, and then the HOM-captor changed blue color was obtained. The HOM-captor changed blue color (solid) adsorbs arsenic but does not almost adsorb the other metal. There is not almost arsenic ion in the filtrate which the HOM-captor changed blue color was removed from, and the concentration of the other metal ions in the filtrate does not almost change. It is proved that the alumina-captor of the present invention does not almost adsorb metal ions except arsenic ion, and that it can adsorb arsenic ion much selectively and much preferentially.

Example 16

Effect of No Heating Regarding as (V) Adsorption

As mentioned above, the optimum conditions for recovering As(V) require heating to 45° C. because the heating enhances the extraction of As(V) and decreases the time of the extraction. However, since equipments and energy are needed to heat, they increase a recovery cost. So, we investigated methods to increase the amount of As(V) recovered at room temperature. It was found that the increase of the amount of As(V) recovered at room temperature can be achieved by lengthening the contact time between alumina-captor and As(V) ion. In the case of contacting them for period of time (60~75 min), the recovery efficiency of As(V) without heating (that is, at room temperature) was about 20% lower than that with 45° C. heating.

Figure 23:
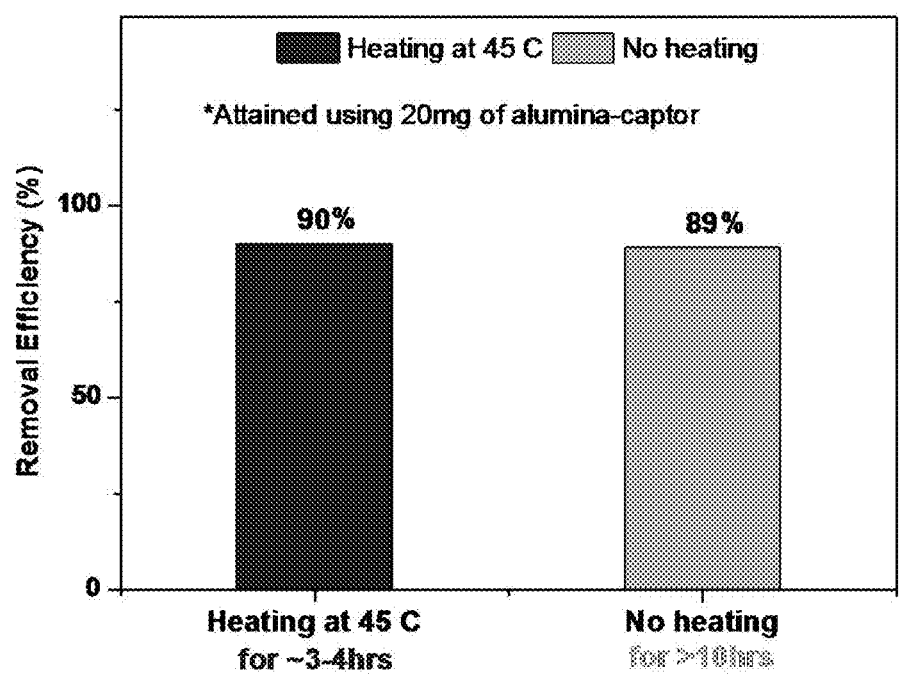
FIG. 23 shows the effects of heating and contact time that affect the removal efficiency of arsenic ion using the alumina-captor.

FIG. 23 shows the effects of heating and contact time that affect the removal efficiency of arsenic ion using alumina-captor. As with the example 13, 20 mg alumina-captor was added in the solution containing arsenic ion, and the arsenic ion was removed from the solution by adsorbed to the alumina-captor with or without heating. The arsenic ion concentration in the solution was measured by ICP-OES to compare it before and after the adsorption of arsenic ion. Then the removal efficiency of arsenic ion was calculated from the result. The vertical axis of FIG. 23 is the removal efficiency of arsenic ion. The removal efficiency of arsenic ion was 90% in the case where arsenic ion contacted with alumina-captor in the solution during about 3 hours under 45° C. heating. The removal efficiency of arsenic ion was 89% in the case where arsenic ion contacted with alumina-captor in the solution during over about 10 hours at room temperature (0-40° C.). Namely, it was recognized that the removal efficiency could be increased by long-time contact between alumina-captor and arsenic ion in the solution in the case of no heating. Heating equipments and facilities are not needed in the case of no-heating. We can recover the comparable amount of arsenic with the amount of arsenic in the case of heating by soaking the alumina-captor in the solution overnight at room temperature, that is, by stirring the solution when the facilities are rested.

Example 17

Effects of Ascorbic Acid Addition

As mentioned above, ascorbic acid was added as essential part for recovering As(V). However, the extra treatment is needed to treat the ascorbic acid as waste. That is, since the amount of chlorine consuming increases to purify a drinking water, the effect of the absence of ascorbic acid on the removal efficiency was investigated. It was found clearly that ascorbic acid, absolutely, has no effect on the removal efficiency of As(V) and its main role is labeling the arsenate-molybdenate-complex indicating its formation with the naked-eye.

Figure 24:
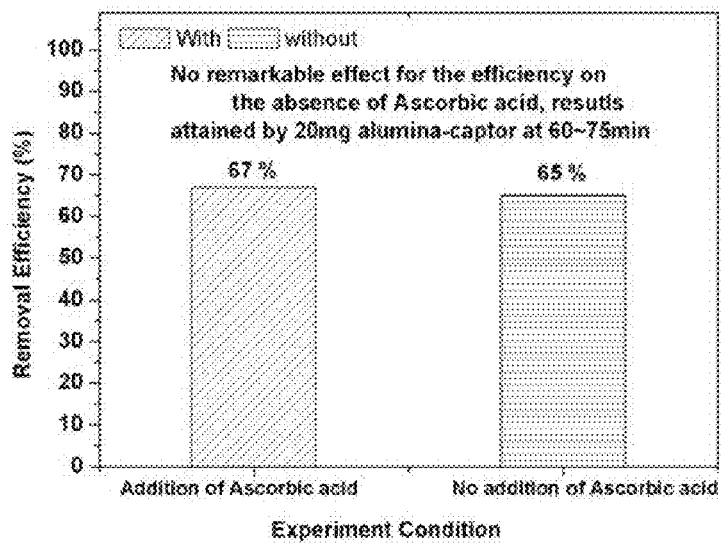
FIG. 24 shows a difference of the extraction efficiency of arsenic ion with or without ascorbic acid.

FIG. 24 shows a difference of extraction efficiency with or without ascorbic acid, namely the effect of ascorbic acid affecting the removal efficiency of As(V) from the solution. In the Example 13, the effect of arsenic removal by the alumina-captor was investigated. 20 mg alumina-captor contacted with the solution containing arsenic ion for 60-75 min. The removal efficiency of arsenic ion by alumina-captor was 67% in the case of addition of ascorbic acid. The removal efficiency of arsenic ion by alumina-captor was 65% in the case of no addition of ascorbic acid. The results show clearly that ascorbic acid does not have a remarkable effect of removing As(V).

Figure 25:
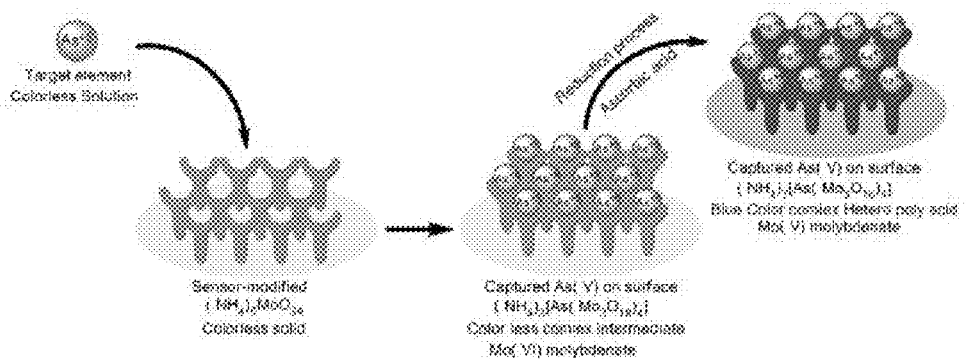
FIG. 25 shows a schematic design to explain the role as a labeling agent of ascorbic acid that has the effect to change color by the arsenic ion adsorption of the heteropoly acid of the invention.

FIG. 25 shows a schematic design to explain the role as a labeling agent of ascorbic acid that changes blue color by the arsenic adsorption of the heteropoly acid (complexation) to the extent that it can be recognized by naked eye, in the system adsorbing arsenic ion using the alumina-captor supporting heteropoly acid of the present invention. In other words, FIG. 25 illustrates the proposed mechanism for capturing As(V) and the role of ascorbic acid in labeling the formed complex only. The alumina-captor, which is the alumina supporting ammonium molybdate (($NH_4)_6MoO_{24}$) that is one of the heteropoly acids, contacted with the solution dissolving arsenic ion of the target element. Arsenic ion was adsorbed and incorporated to the heteropoly acid. As a result, Arscenate-molybdenate-complex was formed. The complexation was carried out in the state where ammonium molybdate (($NH_4)_6MoO_{24}$) was supported on surface of alumina. The captor adsorbing arsenic was $(NH_4)_3[As(Mo_3O_{10})_4]$ complex, and the valence of molybdenum was 6 {Mo(VI)}. The complex (intermediate) shows colorless at this stage. By contacting with ascorbic acid, the complex supported on surface of alumina changed to $(NH_4)_7[As(Mo_3O_{10})_4]$ complex. Namely, molybdenum in the molybdate was reduced and changed to pentavalent molybdenum {Mo(V)}. As a result, the heteropoly acid changed blue color.

Example 18

Applicability to Tap Water of Alumina-Captor

One of the great advantages of our new specially designed alumina-captor is that it does not need any sophisticated conditions related to water source, pH conditions, as well as the contents of the water. So, the applicability to tap water of the alumina-captor was investigated.

The deionized water (DW) was replaced by a spiked tap water to investigate the effect of other ions and additives that may potentially exist in usual tap water. The optimum conditions for removing As(V) from tap water was summarized as follows.

(1) To 50 ml caped flat bottomed bottle equipped with magnetic stirrer, 17.6 ml tap water, 0.4 ml of 100 ppm As(V) solution, and 20 mg alumina-captor were added.

(2) The mixture was stirred well using the magnetic stirrer for 70 min.

(3) After the incubation period (30 min) was finished, 2 ml of 0.1M ascorbic acid was added to the solution and As(V) concentration in the solution was led to about 2 ppm.

(4) Stirring was continued for more 30-40 min, where the blue color observed indicated the detection of the As(V) by the alumina-collector.

(5) The solid was filtered using filter paper GF/C 25 mm ø circles supplied by Whatman™, and washed with a deionized water.

(6) It is found that a clear blue alumina-collector of the solid obtained adsorbed arsenic ion. This indicated the success of collecting the As(V) from the solution.

(7) Arsenic {As(V)} ion concentrations in the solution were measured at each stage by the ICP-OES. Their data is shown in FIG. 26.

As shown in FIG. 26, the arsenic ion concentration in the tap water was much low and 0.0005 ppm. After the aqueous water containing arsenic ion was added to the tap water, the arsenic ion concentration in the solution was 2.013 ppm. Next, after the alumina supporting sodium molybdate (alumina-captor), which is the heteropoly acid and the arsenic ion-adsorption compound, was soaked in the solution, the alumina-captor adsorbing arsenic ion was filtered, and the arsenic ion concentration of the filtrate was 0.685 ppm. As a result, the arsenic ion concentration in the solution removed by the alumina-captor of the present invention was 1.328 ppm. That is, the removal efficiency of arsenic was about 66%.

Example 19

Applicability to Natural Waste Water of Alumina-Captor

Figure 28:
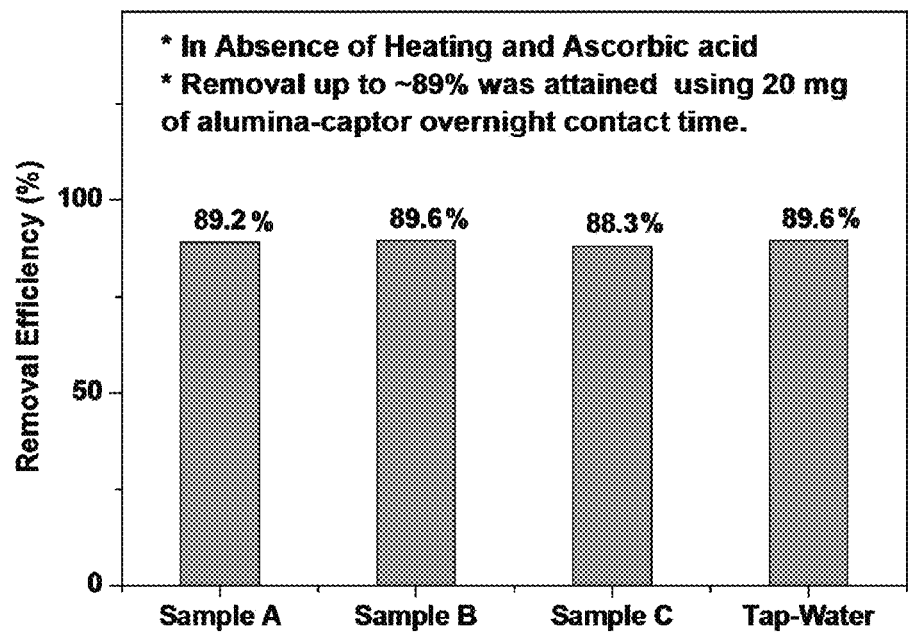
FIG. 28 is a graph that shows the removal efficiency of arsenic by the alumina-captor in the natural water.

The efficiency of the alumina-captor as highly selective removal agent for As(V) was also investigated in natural water. Three different samples were brought from different sites in a lake of Tsukuba-city in Ibaraki-prefecture in Japan. The three samples were tested against 20 mg alumina-captor in absence of heating and ascorbic acid because of the low cost. After the alumina-captor was soaked in the sample solution, they were stirred for overnight to attain higher removal efficiency because of the absence of heating. It was confirmed that the alumina-captor of the present invention, which is a new innovative system, can be available in the natural field water source. The test procedure was the same as that of Example 18. The tap water was replaced by the sample solution. Heating and ascorbic acids were not used. Arsenic {As(V)} ion concentration in each sample solution was measured with ICP-OES at each stage. The ICP data were summarized is shown in FIGS. 27 and 28. FIG. 27 is a table that shows an arsenic {As(V)} ion concentration and a removal efficiency of arsenic before and after the alumina-captors in the natural water were processed. FIG. 28 is a graph made from the table, namely, shows the removal efficiency of arsenic by the alumina-captor in the natural water. The vertical axis in FIG. 28 is the removal efficiency of arsenic.

The arsenic {As(V)} ion concentrations of all the samples were below 0.0007 ppm before each sample solution containing tap water solution was treated. The arsenic {As(V)} ion concentrations were 2.011 ppm to 2.014 ppm after the solution containing arsenic ion was added to the each sample solution. The arsenic {As(V)} ion concentrations of the filtrate were 0.2147 ppm to 0.2350 ppm after the alumina-captor of the present invention was added to the sample solution and adsorbed arsenic ion and filtered. The removal efficiencies for all the samples were 88.3% to 89.6%. These were about 22% higher than the removal efficiencies of Examples 18 etc. This is the effect by mainly the absence of heating, namely, the effect for overnight at room temperature. This result suggests that the removal efficiency increases further by the optimization of heating conditions. Since ascorbic acid is not used, the alumina-captor adsorbing arsenic did not change blue color, unlike Example 19. This indicates that the filtrate can be directly returned to drinking water, agricultural water and daily life water, etc. without treating ascorbic acid in the filtrate.

Figure 29:
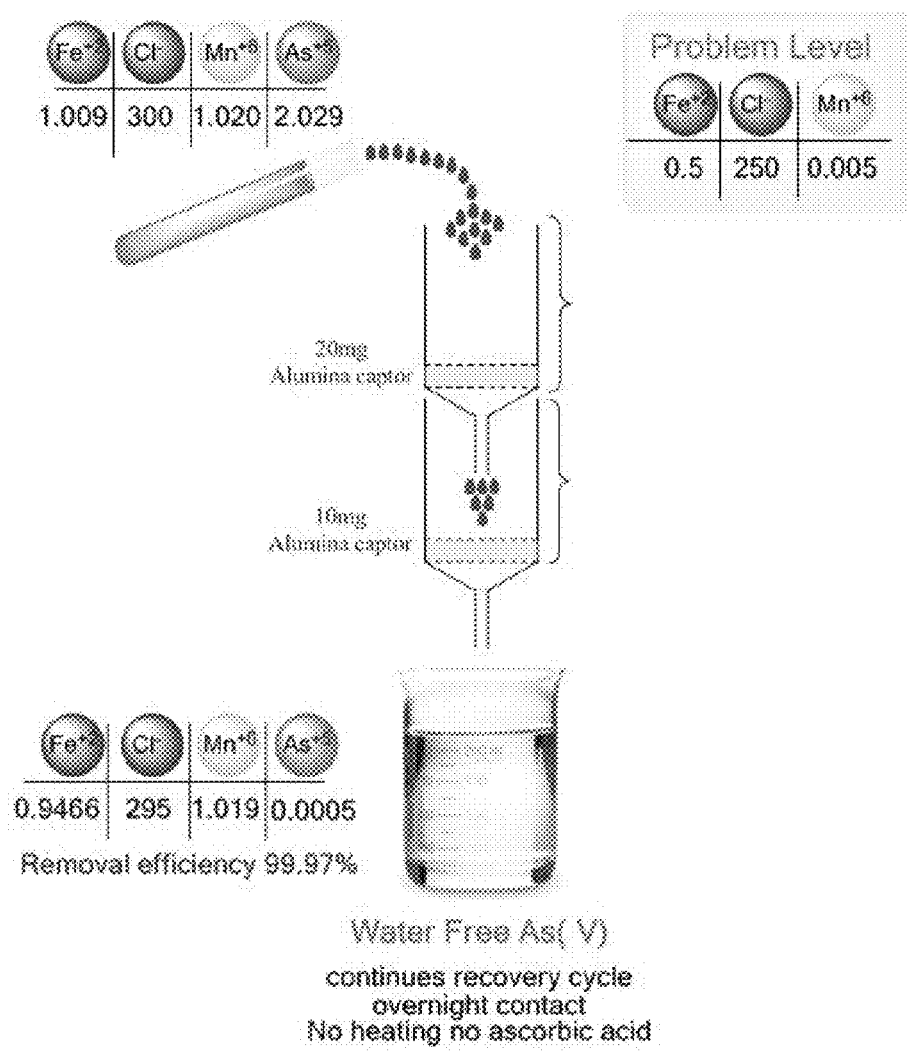
FIG. 29 shows a continuous arsenic recovery system that achieves the arsenic-free drinking water using the alumina-captor of the present invention.

FIG. 29 shows a continuous arsenic recovery system that achieves arsenic-free solution using the alumina-captor of the present invention. Two reservoirs, in which the alumina-captor of the present invention is put, are arranged one above the other. Firstly, ion solution dissolving various anions and cations (metal ion etc.) is put into the upper reservoir and then is kept for a fixed time. The solution in the upper reservoir is well stirred and the alumina-captor sufficiently contacts with the solution. After the fixed time passes, the ion solution in the upper reservoir is transferred into the under reservoir. If a valve is equipped between the upper reservoir and the under reservoir, since the solution in the upper reservoir drops gravitationally and naturally by opening of the valve, the transfer of the solution does not need energy.

Since the alumina-captor of the present invention in the upper reservoir adsorbs arsenic in the ion solution containing arsenic ion, cations and anions, the arsenic ion concentration in the ion solution discharged from the upper reservoir is reduced considerably. In the case that the arsenic ion concentration in the ion solution poured initially was 2.029 ppm (Ferric ion, chlorine ion and manganese ion in the solution were also contained.), after contacting for overnight, arsenic ion concentration in the ion solution discharged from the upper reservoir is about 0.223 ppm from the removal efficiency (about 89%) obtained in Example 19. Since alumina-captor of the present invention is put in the under reservoir, the alumina captor can contact well (for example, using a stirrer) with the ion solution poured from the upper reservoir into the under reservoir. After the alumina-captor contacts with the ion solution for fixed time in the under reservoir, the ion solution is discharged from the under reservoir. Since the alumina-captor of the present invention adsorbs arsenic in the ion solution, the arsenic ion concentration in the ion solution discharged from the under reservoir is reduced considerably. In the case that the arsenic ion concentration in the ion solution transferred from the upper reservoir is about 0.223 ppm, after overnight contacting, the arsenic ion concentration in the ion solution discharged from the under reservoir is about 0.025 ppm. Accordingly, even though the arsenic ion concentration of the initial solution is 2 ppm and high, the arsenic ion concentration in the solution treated using the two steps continuous arsenic recovery system of the present invention shown in FIG. 29 becomes below 0.1 ppm and is harmless to humans. In the real data, the arsenic ion concentration in the solution was about 0.005 ppm, as shown in FIG. 29. But the concentration of the other ions did not almost change. Only arsenic was removed from the solution. Then, the removal efficiency of arsenic was about 99.97%, and the much low level of the arsenic ion concentration in the solution can be achieved.

The solution having the lower arsenic concentration can be obtained by connecting the more reservoirs in which the alumina-captor of the present invention can be put, as shown in FIG. 29. Especially as shown in FIG. 21, since the alumina-captor of the present invention can adsorb ultratrace of arsenic ion less than 1 ppb, even though the arsenic concentration in the initial solution is very high, arsenic-free solution having the lower arsenic concentration than 1 ppb can be prepared using simple equipments without taking much time by using multi continuous arsenic recovery system. Since the alumina-captors do not adsorb arsenic ion beyond the maximum adsorption level, when the arsenic concentration of them approaches the maximum adsorption levels, they may be exchanged for the new alumina-captors that are not adsorbing arsenic ion. And then, since the arsenic ion concentration can be seen by the blue color strength in the solution containing the ascorbic acid, the alumina-captor can be exchanged easily. However, the inclusion of ascorbic acid in the solution means that the removal of the ascorbic acid from the solution to reuse the solution must be considered. So, the exchange time of the alumina-captor can be determined without ascorbic acid by obtaining the data previously. Or the exchange period of the alumina-captor can be known without ascorbic acid by equipping the system with the feature measuring the arsenic concentration in the solution using ICP-OES, etc. Or if some of the solution is taken into test tube, the arsenic concentration in the test tube can be measured. From the above, even though the treatment at room temperature (0-40, preferably 20-40° C.) without heating and/or ascorbic acid are carried out, the arsenic-free solution having the arsenic ion concentration below the target limit can be prepared by using the plural continuous arsenic removal system such as the system in FIG. 29.

Other advantage of the multi continuous arsenic removal system shown in FIG. 29 is that the time to keep ion solution in one reservoir can be shorten by the multi connection of reservoirs. Accordingly, a large amount of solution can be treated, and the removal cost of arsenic ion in the solution decreases considerably since the equipments are also cheap. Furthermore, we can treat a larger amount of solution at lower cost by using the alumina-captor of the present invention in a continuous fluid bed system that develops the multi system. We can construct the arsenic ion removal system or the arsenic ion removal equipments such as the system in FIG. 29 by using the mesoporous alumina supporting arsenic ion-absorbing compound of the present invention as the arsenic ion adsorption material used in the environment. We can reuse the solution in which arsenic ion is removed as a drinking water, a daily life water, an agricultural water, or an industrial water by removing arsenic ion from the arsenic ion solution such as well water, natural water such as river or lake, ditch before clarification, industrial effluent, or living drainage. (Of course, the removal of the other ions is also needed.) In the case that ferric ion ($Fe^{+2}$), chlorine ion ($Cl^{-1}$), manganese ion $Mn^{+6}$), etc. shown in FIG. 29 are removed, the materials removing these ions may be added together with the mesoporous alumina supporting the arsenic ion adsorption materials in the solution.

Figure 30:
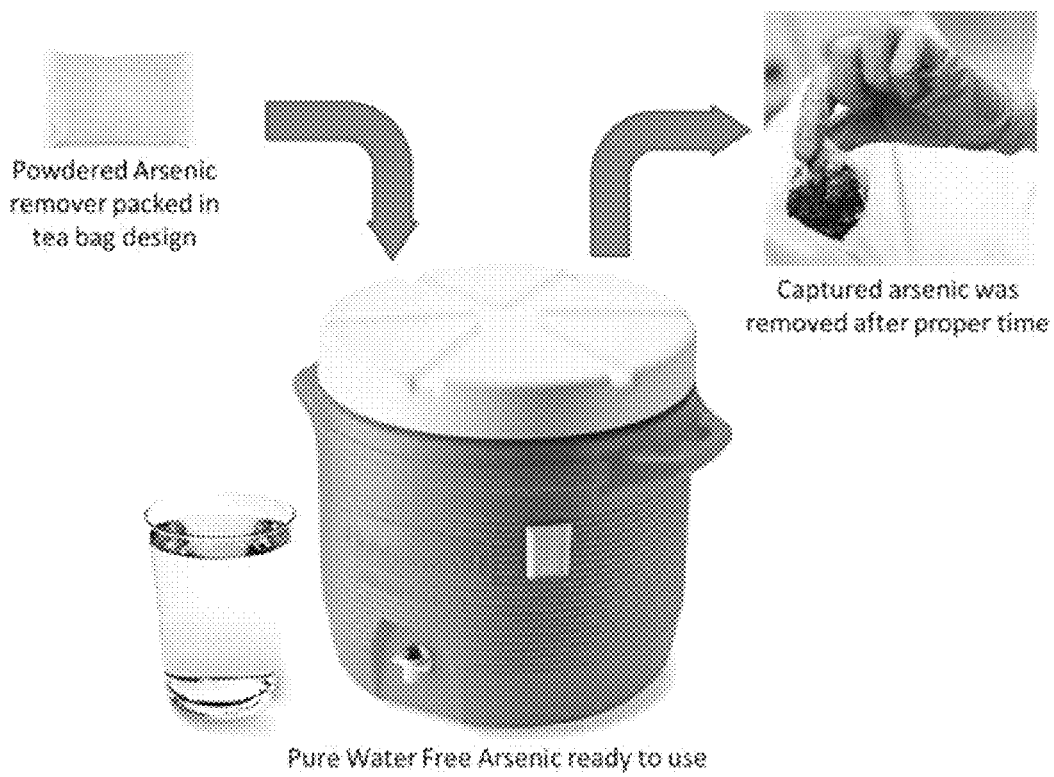
FIG. 30 shows a system to supply the arsenic-free drinking water obtained by removing arsenic ion by adsorbing arsenic ion from home drinking water.

FIG. 30 shows a system supplying a arsenic-free drinking water obtained by removing arsenic ion by adsorbing arsenic ion from home drinking water. The alumina-captor of the invention is put in a tea-bag, and the tea bag is put in the drinking water. Since even trace of arsenic ion enhances carcinogenic property by long-term consumption, even ultra trace of arsenic ion should be desirably removed. It is difficult for traditional depleting materials of arsenic to remove ppb level of arsenic. However, since the alumina-captor can adsorb ultra trace of arsenic ion in ppb-ppt level, arsenic-free drinking water can be supplied. For example, as shown in FIG. 30, if the alumina-captor is put instead of tea in a bag like tea-bag, and the bag is put as an arsenic adsorption bag in a drink container, we can drink arsenic-free water. Namely, the arsenic adsorption bag can be used as arsenic adsorption material. Since the arsenic ion adsorption compound supported by alumina combines strongly with the alumina, it does not separate from the alumina during use and it does not dissolve in the water. Accordingly, the arsenic adsorption bag can be used much safely. If arsenic ion dissolves at ppm level in the drinking water, our life is in danger. However, owing to the arsenic adsorption bag put in the drinking water, the arsenic concentration decreases below the concentration that affects human body. If the arsenic adsorption bag spent is treated by alkaline solution, arsenic ion adsorbed by the alumina-captor can be dissolved by the alkaline solution. Accordingly, the arsenic adsorption bag can be reused. Arsenic-free drinking water can be supplied easily in home using a small bag (an arsenic adsorption bag) in which the mesoporous alumina supporting the arsenic ion adsorption compound is put. Furthermore, since the arsenic adsorption bag can be reused repeatedly, the arsenic-free drinking water supply system of this invention using small bags (arsenic adsorption bags) is economic and low in cost.

In the present invention, the arsenic ion adsorption compound is supported by the mesoporous alumina. For example, we make ammonium molybdate support the mesoporous alumina by mixing the mesoporous alumina, which is obtained after reacting a surfactant to the mesoporous alumina, in the solution containing the ammonium molybdate. The mesoporous alumina supporting the arsenic ion adsorption compound such as the ammonium molybdate can remove trace of arsenic ion in the water by selectively adsorbing it with a room temperature process without water conditioning such as pretreatment or posttreatment such as pH adjustment. Accordingly, since our removal system of arsenic-ion does not need an extra posttreatment not to execute a special pre-treatment (for example, acid treatment or alkali treatment) and does not use heating equipment, the system cost is low. Furthermore, since our system can construct multistage structures, it can obtain arsenic-free water solution, which can be used for a drinking water or daily life water, rapidly and liberally and cheaply. In addition, since the mesoporous alumina supporting arsenic ion adsorption compound can extract and collect arsenic ion in the solution, it can be used as arsenic collector (that is, alumina-collector or alumina-captor). Moreover, our mesoporous alumina supporting arsenic ion adsorption compound can be used as an arsenic ion-sensor, which detects arsenic ion in the solution, since it changes color at ppm-ppb-ppt level of arsenic concentration in the case of adding the ascorbic acid in the solution. Also, our mesoporous alumina supporting arsenic ion adsorption compound can be used as a filter that can remove arsenic ion at ppm-ppb-ppt level of arsenic concentration. The arsenic-free water can be supplied always by fitting our filter to a supply inlet of home drinking water or industrial water.

In the case that the contents written in the present application are compatibly applicable to the part of the application in which they are not written, it goes without saying that they can apply to the said part. Also, since the embodiments and the examples written in the present application are one or some of many examples of the present invention, it will be obvious to those skilled in the art that they can be conducted or practiced by changing in various ways without departing from the scope of the invention, and that the scope of right of the invention is not limited to the embodiments and the examples mentioned above.

INDUSTRIAL APPLICABILITY

This invention can be utilized in the industrial fields regarding arsenic ion collectors and arsenic ion sensors, in the industrial fields where arsenic ions are removed from substances and materials containing various cations, anions, surfactants, etc., and in the industrial fields where arsenic is recovered and drinking water is purified.

What is claimed is:

1. A nanostructure material supporting an arsenic ion adsorption compound that can adsorb an arsenic ion from an arsenic ion solution of a target element, and that can separate the arsenic ion adsorbed:
    wherein the nanostructure material is selected from the group consisting of a titania nanotube, a zinc oxide nanorod and an alumina nanorod; and
    wherein the arsenic on adsorption compound is an ammonium molybdate.

2. The nanostructure material according to claim 1, wherein the titania nanotube is made by adding an ethanol and a surfactant F108 to a mixed solution of titanyl sulfate ($TiSO_4$), an ethanol and a sulfuric acid aqueous solution.

3. The nanostructure material according to claim 1, wherein the zinc oxide nanorod is made by adding a surfactant cetyltrimethyl ammonium bromide (CTAB) to a zinc chloride ($ZnCl_2$) aqueous solution.

4. The nanostructure material according to claim 1, wherein the alumina nanorod is made by adding a surfactant cetyltrimethyl ammonium bromide (CTAB) to an aluminum nitrate $\{Al(NO_3)_3\}$ aqueous solution.

5. The nanostructure material according to claim 1, wherein the ammonium molybdate is supported by the nanostructure material by mixing the nanostructure material in an aqueous solution containing the ammonium molybdate after the nanostructure material is treated by a surfactant.

6. The nanostructure material according to claim 5, wherein the surfactant is a dilauryl dimethyl ammonium bromide (DDAB).

7. A method for detecting arsenic ion concentration in an aqueous solution, wherein the method comprises:
    putting the nanostructure material according to claim 1 in an acid aqueous solution and stirring the add aqueous solution,
    filtering the acid aqueous solution,
    recovering and drying the nanostructure material, and
    measuring spectroscopic characteristics of the nanostructure material.

8. A method for removing an arsenic ion in an aqueous solution, wherein the method comprises:
    putting the nanostructure material according to claim 1 in an acid aqueous solution and stirring the acid aqueous solution,
    separating and removing the nanostructure material supporting the arsenic ion adsorption compound from the acid aqueous solution, and
    obtaining the acid aqueous solution from which the arsenic ion has been removed.

9. A method for recovering the nanostructure material supporting the arsenic ion adsorption compound, which is adsorbing the arsenic ion, used in the method for detecting arsenic ion concentration according to claim 7, wherein the method further comprises:
    putting and stirring the nanostructure material, which is adsorbing the arsenic ion, in an alkali solution, and
    eluting the arsenic ion adsorbed by the nanostructure material in the alkali solution.

10. The method for removing the arsenic ion in the aqueous solution, using the nanostructure material supporting the arsenic ion adsorption compound recovered according to claim 9.

11. The method for detecting the arsenic ion in the aqueous solution, using the nanostructure material supporting the arsenic ion adsorption compound recovered according to claim 9.

12. A mesoporous alumina supporting an arsenic ion adsorption compound that can adsorb an arsenic ion of a target element from an arsenic ion solution, and that can separate the arsenic ion adsorbed, wherein the mesoporous alumina is made using an aluminum nitrate and a surfactant.

13. The mesoporous alumina according to claim 12, wherein the surfactant is selected from the group consisting of a camphorsulfonic acid (CSA) and a surfactant cetyltrimethyl ammonium bromide (CTAB).

14. A mesoporous alumina supporting an arsenic ion adsorption compound that can adsorb an arsenic ion from an arsenic ion solution of a target element, and that can separate the arsenic ion adsorbed, wherein the mesoporous alumina is made by a hydrolysis of an aluminum isopropoxide ($C_9H_{21}AlO_3$).

15. The mesoporous alumina according to claim 12, wherein the arsenic ion adsorption compound can selectively adsorb an arsenic ion of a target element.

16. The mesoporous alumina according to claim 12, wherein the arsenic ion adsorption compound is a heteropoly acid.

17. The mesoporous alumina according to claim 16, wherein the heteropoly acid is ammonium molybdate.

18. The mesoporous alumina according to claim 17, wherein the ammonium molybdate is supported by the mesoporous alumina by mixing a solid alumina, which is obtained after reacting a surfactant to the mesoporous alumina, in the solution including the ammonium molybdate.

19. The mesoporous alumina according to claim 17, wherein a temperature at which the ammonium molybdate supported by the mesoporous alumina adsorbs arsenic ion is room temperature.

20. The mesoporous alumina according to claim 17, wherein at least one of a pretreatment or a posttreatment is not carried out when the ammonium molybdate supported by the mesoporous alumina adsorbs arsenic ion by contacting with the arsenic ion solution.

21. The mesoporous alumina according to claim 12, wherein a concentration of the arsenic ion adsorbed is determined by a color using an ascorbic acid when the arsenic ion adsorption compound supported by the mesoporous alumina adsorbs arsenic ion by contacting with the arsenic ion solution.

22. A method for detecting the arsenic ion concentration in the arsenic ion solution, wherein the concentration of the arsenic ion adsorbed is determined by a color using an ascorbic acid when the arsenic ion adsorption compound supported by the mesoporous alumina according to claim 12 adsorbs arsenic ion by contacting with the arsenic ion solution.

23. A collector for collecting arsenic (As) using the mesoporous alumina according to claim 12.

24. A filter for removing arsenic (As) using the mesoporous alumina according to claim 12.

25. An agent for adsorbing arsenic (As) using the mesoporous alumina according to claim 12.

26. The agent for adsorbing arsenic (As) according to claim 24, wherein the agent is present in a bag.

27. A system for removing arsenic ion, wherein the system can remove the arsenic ion from the arsenic ion solution using the mesoporous alumina according to claim 12, and the water from which the arsenic ion is removed is usable as at least one of drinking water, agricultural water and industrial water.

28. An equipment for removing the arsenic ion, wherein the equipment can remove the arsenic ion by mixing the arsenic ion solution and the mesoporous alumina supporting the arsenic ion adsorption compound according to claim 12 in the equipment.

29. The equipment for removing the arsenic ion according to claim 28, wherein the arsenic ion concentration in the arsenic ion solution is reduced by less than a constant concentration by multiple contacts between the arsenic ion solution and the mesoporous alumina supporting the arsenic ion adsorption compound by connecting plural of the equipments serially.

30. A method for recovering arsenic using a mesoporous alumina comprising:
 a process in which an arsenic ion adsorption compound is supported by the mesoporous alumina,
 a process in which the mesoporous alumina supporting the arsenic ion adsorption compound contacts with an arsenic ion solution, and
 a process in which arsenic ion is selectively adsorbed by the arsenic ion adsorption compound supported by the mesoporous alumina,
 wherein the arsenic on adsorption compound is a heteropoly acid.

31. The method for recovering arsenic according to claim 30, further comprising a process in which the arsenic ion adsorbed is separated from the arsenic ion adsorption compound.

32. The method for recovering arsenic according to claim 30, wherein the mesoporous alumina supporting the arsenic ion adsorption compound can be reused.

33. The method for recovering arsenic according to claim 30, wherein the heteropoly acid is ammonium molybdate.

34. The method for recovering arsenic according to claim 33, wherein the ammonium molybdate is supported by the mesoporous alumina by mixing the solid alumina, which is obtained by reacting the mesoporous alumina to a surfactant, in the solution containing the ammonium molybdate.

35. The method for recovering arsenic according to claim 33, wherein a temperature to adsorb the arsenic ion by contacting between the mesoporous alumina supporting the ammonium molybdate and the arsenic ion solution is room temperature.

36. The method for recovering arsenic according to claim 33, wherein at least one of a pretreatment or a posttreatment is not carried out when the ammonium molybdate supported by the mesoporous alumina adsorbs arsenic ion by contacting with the arsenic ion solution.

37. The method for recovering arsenic according to claim 33, wherein the concentration of the arsenic ion adsorbed is determined by a color using an ascorbic acid when the ammonium molybdate supported by the mesoporous alumina adsorbs arsenic ion by contacting with the arsenic ion solution.

38. The method for recovering arsenic according to claim 33, further comprising a process in which the arsenic ion adsorbed is separated from the arsenic ion adsorption compound.

39. The method for recovering arsenic according to claim 33, wherein the mesoporous alumina supporting the arsenic ion adsorption compound can be reused.

\* \* \* \* \*